US008481081B2

(12) United States Patent
Babcock et al.

(10) Patent No.: US 8,481,081 B2
(45) Date of Patent: Jul. 9, 2013

(54) PHARMACEUTICAL SOLID DISPERSIONS

(75) Inventors: Walter C. Babcock, Bend, OR (US);
Dwayne T. Friesen, Bend, OR (US);
James A. S. Nightingale, Bend, OR (US); Ravi M. Shanker, Groton, CT (US)

(73) Assignee: Bend Research, Inc., Bend, OR (US)

( * ) Notice: Subject to any disclaimer, the term of this patent is extended or adjusted under 35 U.S.C. 154(b) by 394 days.

(21) Appl. No.: 10/459,808

(22) Filed: Jun. 10, 2003

(65) Prior Publication Data

US 2004/0013734 A1   Jan. 22, 2004

Related U.S. Application Data

(63) Continuation of application No. 09/495,049, filed on Jan. 31, 2000, now abandoned.

(60) Provisional application No. 60/119,401, filed on Feb. 10, 1999.

(51) Int. Cl.
*A61K 9/14* (2006.01)

(52) U.S. Cl.
USPC ......................................................... 424/488

(58) Field of Classification Search
USPC ......................................................... 424/484
See application file for complete search history.

(56) References Cited

U.S. PATENT DOCUMENTS

| 3,449,489 | A |   | 6/1969  | Gaunt et al. ................. 424/31 |
| 4,343,789 | A | * | 8/1982  | Kawata et al. ............... 514/356 |
| 4,404,183 | A |   | 9/1983  | Kawata et al. ................ 424/19 |
| 4,673,564 | A |   | 6/1987  | Kawata et al. ............... 424/494 |
| 4,835,186 | A |   | 5/1989  | Reuter et al. ................ 514/570 |
| 4,983,593 | A |   | 1/1991  | Miyajima et al. ............ 514/110 |
| 5,098,893 | A |   | 3/1992  | Franks et al. ................. 514/54 |
| 5,340,591 | A |   | 8/1994  | Nakano et al. ............... 424/499 |
| 5,456,923 | A |   | 10/1995 | Nakamichi et al. .......... 424/489 |
| 5,700,485 | A |   | 12/1997 | Berde et al. ................. 424/501 |
| 5,723,269 | A |   | 3/1998  | Akagi et al. ................. 424/497 |
| 5,928,469 | A |   | 7/1999  | Franks et al. ............... 159/48.1 |
| 5,935,939 | A |   | 8/1999  | Kararli et al. ................. 514/54 |
| 5,945,127 | A |   | 8/1999  | Breitenbach et al. ........ 424/489 |
| 5,985,313 | A | * | 11/1999 | Neurath et al. .............. 424/434 |

FOREIGN PATENT DOCUMENTS

| DE | 19509806    |   | 9/1996  |
| DE | 19800927    |   | 7/1999  |
| EP | 0784974     | * | 7/1997  |
| EP | 0901786     |   | 3/1999  |
| EP | 0988863     |   | 3/2000  |
| EP | 1027886     |   | 8/2000  |
| EP | 0784974 B1  |   | 5/2003  |
| EP | 1070725 B1  |   | 9/2010  |
| GB | 0742554     |   | 12/1955 |
| JP | S61-227524 A|   | 10/1986 |
| WO | WO 9001329  |   | 2/1990  |
| WO | WO 9300889  | * | 1/1993  |
| WO | WO 9638153  |   | 12/1996 |

OTHER PUBLICATIONS

Beten et al. Preparation of controlled-release co-evaporates of dipyridamole by loading neutral pellets in a fluidized-bed coating system. Pharm Res. Sep. 1995; 12(9):1269-72.*
Abd et al (Preparation and Pharmacokinetic Evaluation of Carbamazepine Controlled Release Solid Dispersion Granules, J. Drug Res. Egypt, 22, 1-2(1998). p. 15-31).*
Takenaka et al (Preparation of enteric-coated microcapsules for tableting by spray-drying technique and in vitro simulation of drug release from the tablet in GI tract. J Pharm Sci. Dec. 1980;69(12):1388-92).*
Leuner, et al., European Journal of Pharmaceutics and Biopharmaceutics, 50, 2000, pp. 47-60.
Dordunoo, et al., Drug Development and Industrial Pharmacy, 17(12), 1991, pp. 1685-1713.
Wan, et al., Drug Development and Industrial Pharmacy, 18(9), 1992, pp. 997-1011.
Yuasa, et al., Chem. Pharm. Bull, 42(2), 1994, pp. 354-358.
Giunchedi, et al., International Journal of Pharmaceutics, 85, 1992, pp. 141-147.
Xu, et al., Pharmaceutical Research, vol. 10, No. 8, 1993, pp. 1144-1152.
Sheen, et al., International Journal of Pharmaceutics, 118, 1995, pp. 221-227.
Sjokvist, et al., International Journal of Pharmaceutics, 79, 1992, pp. 123-133.
Ford, Pharm. Acta Helv, 61, No. 3, 1986, pp. 69-86, "The Current Status of Solid Dispersions".
Chiou, et al., Journal of Pharmaceutical Sciences, vol. 58, No. 12, Dec. 1969, pp. 1505-1510.
Hasegawa, et al., Chem. Pharm. Bull, 33(1), 1985, pp. 388-391.
Dangprasirt, et al., Drug Development and Industrial Pharmacy, 21(20), 1995,pp. 2323-2337.
Giunchedi, et al., Drug Development and Industrial Pharmacy, 21(3), 1995, pp. 315-330.
Giunchedi, et al., J. Microencapsulation, 1996, vol. 13, No. 1, pp. 89-98.
Hasegawa, et al., Chem. Pharm. Bull., 33(8), 1985, pp. 3429-3435.
Takenaka, et al., Journal of Pharmaceutical Sciences, vol. 69, Dec. 1980, pp. 1388-1392.
Takeuchi, et al., Chem. Pharm. Bull., 35(9), 1987, pp. 3800-3806.
Toshlya, et al., Chem. Pharm. Bull, 44(3), 1996, pp. 568-571.
Lakellariou et al, "The Thermomechanical Properties and Glass Transition Temperatures of Some Cellulose Derivatives used in Film Coating," International Journal of Pharmaceutics, 27(1985)267-277.
Abd et al, "Preparation and Pharmacokinetic Evaluation of Cabamazepine Controlled Release Solid Dispersion Granules," Journal of Drug Research Egypt, 22, 1-2(1998)15-31.

* cited by examiner

*Primary Examiner* — Jake Vu
(74) *Attorney, Agent, or Firm* — Chernoff Vilhauer McClung & Stenzel LLP

(57) ABSTRACT

A composition comprises a solid dispersion comprising a low-solubility drug and at least one polymer. At least a major portion of the drug in the dispersion is amorphous. The polymer has a glass transition temperature of at least 100° C. measured at a relative humidity of fifty percent. Another aspect of the invention comprises the same composition except that the dispersion has a glass transition temperature of at least 50° C. at a relative humidity of fifty percent. In another aspect of the invention, a composition comprises a solid dispersion comprising a low-solubility drug and a stabilizing polymer. At least a major portion of the drug in the dispersion is amorphous. The composition also includes a concentration-enhancing polymer that increases the concentration of the drug in a use environment. The stabilizing polymer has a glass transition temperature that is greater than the glass transition temperature of the concentration-enhancing polymer at a relative humidity of 50%.

3 Claims, 3 Drawing Sheets

PHARMACEUTICAL SOLID DISPERSIONS

The priority date of Provisional Application Ser. No. 60/119,401 filed Feb. 10, 1999 is claimed.

BACKGROUND OF THE INVENTION

Low-solubility drugs often show poor bioavailability or irregular absorption, the degree of irregularity being effected by factors such as dose level, fed state of the patient, and form of the drug. Increasing the bioavailability of low-solubility drugs has been the subject of much research. Increasing bioavailability hinges on improving the concentration of the drug in solution to improve absorption.

It is known that solid amorphous dispersions comprising a low-solubility drug in a polymer can increase the maximum concentration of drug that will dissolve in an aqueous solution in in vitro tests, or that will dissolve in body fluids such as those present in the gastrointestinal (GI) tract in in vivo tests, and, in turn, enhance the bioavailability of the drug. Solid dispersions of a drug in a matrix such as a polymer-can be prepared, for example, by forming a homogeneous solution or melt of the drug in matrix material, followed by solidifying the mixture by cooling or removal of solvent. Such solid dispersions of crystalline drugs have been known for more than two decades, and often show enhanced bioavailability when administered orally relative to compositions comprising undispersed crystalline drug.

One method for forming solid dispersions involves spray-drying-the drug and polymer together to form compositions of-drugs and polymers. For example, spray-dried compositions of drugs and polymers have been disclosed by Kai et al., 44 *Chem. Pharm. Bull.* 568-571 (1996); Takeuchi et al., 35 *Chem. Pharm. Bull.* 3800-3806 (1987); Dangprasirt et al., 21 *Drug Development and Industrial Pharmacy*: 2323-2337 (1995); Berde et al., U.S. Pat. No. 5,700,485; Wan et al., 18 *Drug Development and Industrial Pharmacy* 997-1011 (1992); and Akagi, U.S. Pat. No. 5,723,269.

Kai et al. disclose forming solid dispersion systems with an enteric polymer such as hydroxypropyl methylcellulose phthalate (HPMCP) or carboxymethyl ethylcellulose (CMEC), and with the non-enteric polymer hydroxypropylmethylcellulose (HPMC) by spray-drying. The drug is stated to be in an amorphous state. Kai et al. state that it is well-known that the crystallization of a drug within a polymer dispersion can occur during storage of the solid dispersion formulation, resulting in decreased bioavailability. The dispersion was reported to be stable for two months under desiccated storage conditions of elevated temperature (60° C.) in closed glass bottles, meaning that storage was under dry conditions.

Takeuchi et al. disclose an amorphous solid dispersion of tolbutamide in the enteric coating polymers EUDRAGIT® and HPMCP. The solid dispersions were prepared by spray-drying. The drug was stated to be poorly water-soluble. The authors state the amorphous state of the drug was well-maintained under dry conditions. However, the authors noted that the stability of the amorphous state of the drug in the solid dispersion was sensitive to the content of water around or in the sample.

U.S. Pat. Nos. 4,343,789, 4,404,183 and 4,673,564 all have the same disclosure of a sustained release composition of the vasodilator nicardipine comprising a solid amorphous dispersion of the drug in microcrystalline cellulose, polyethylene oxide, polyvinyl pyrrolidone and the cellulosic polymers hydroxypropylcellulose, hydroxypropylmethylcellulose and hydroxypropylmethylcellulose phthalate. However, the preferred method of forming the dispersion is by extensive and time-consuming ball-milling, and there is no recognition of the concentration-enhancing and drug-stabilizing properties of ionizable cellulosics for forming the drug dispersion.

It is also known to form solid dispersions containing polymers by other methods, such as by milling, grinding or solvent evaporation. For example, Nakamichi U.S. Pat. No. 5,456,923 discloses a process for forming solid dispersions using a twin-screw extruder. Nakamichi confirms that the resulting compositions are solid dispersions by noting the disappearance of peaks characterizing crystalline drug in X-ray diffraction analysis. Nakamichi does not discuss the stability of the drug in the dispersion.

Mechanical processes, such as that used by Nakamichi, have several drawbacks. First, the mechanical process normally does not achieve uniform homogeniety of the dispersion. After mixing, while the drug may be in an amorphous state, nevertheless the dispersion may be comprised of drug-rich regions with low concentrations of polymer. Second, the mechanical mixing process can degrade the drug. These two drawbacks are interrelated, since in order to increase the homogeneity of the dispersion, it is necessary to mix for longer periods of time or under more severe conditions of heat and pressure. Longer mixing times or severe conditions often result in greater amounts of degraded drug.

Yuasa et al., 42 *Chem. Phaxm. Bull.* 354-358 (1994) disclose a solid dispersion method used to improve bioavailability of slightly water-soluble drugs. The polymer is hydroxypropylcellulose (HPC). The HPC/drug dispersion is prepared by solvent evaporation, which is then ground and sieved. The authors report that the drug is in an amorphous state in the solid dispersion.

Nakano et al. U.S. Pat. No. 5,340,591 disclose solid dispersions of a sparingly soluble drug and cellulosic polymers. The dispersion is formed by mixing the drug and polymer while heating. The inventors state the drug is in an amorphous state.

Hasegawa et al., 33 *Chem. Pharm. Bull.* 388-91 (1985) disclose a solid dispersion prepared from the solvent evaporation method using the polymer HPMCP.

However, solid dispersions generally have not been used commercially to provide dosing of low-solubility drugs. As recognized by Kai-et al., Takeuchi et al., and Ford, J. L., 61 *Pharm. Acta. Helv.* 75 (1986), a problem encountered by dispersions of low-solubility drugs has been that these dispersions are susceptible to changes during storage and thus are not stable over time. Stability in this context refers to physical stability, that is the tendency for the drug present in a solid amorphous dispersion of drug in polymer to separate into drug-rich domains and/or to convert over time, at least partially, to the crystalline state. Most drug or pharmaceutical formulations are stored at ambient temperatures and relative humidity (atmospheric moisture) which can often be in excess of 50%. Such drug formulations should be as physically stable as possible in such an environment. Stability should be observed for at least one month, but ideally should be observed for a period of time of up to two years in order to provide unchanged bioavailability. Otherwise, such drug formulations require special handling and restrictions on prescriptions and on use by patients.

A major problem with current solid dispersions of drugs is that while the dispersions may show enhanced bioavailability of the low-solubility drug if administered shortly after preparation, bioavailability typically decreases over time in a typical storage environment. Such solid dispersions are often physically unstable in that the the drug present in the dispersion reverts to the crystalline form upon storage-particularly at elevated temperature and humidity. Accordingly, the dispersion cannot be used to provide proper dosing of the drug because the bioavailability of the drug changes over time.

Because of this, numerous researchers have sought to improve the stability of the dispersion. It has been widely thought that stable dispersions might best be obtained by using a matrix material in which the drug was highly soluble, thereby obtaining a thermodynamically stable solid solution. See, for example, Chino et al., 58 *J. Pharm. Scab* . 1505 (1969); Soukis et al., 79 *International J. Pharmaceutics* 120 (1992); Sheen et al., 118 *International J. Pham* . 221 (1995); and Gordano et al. 17 *Drug Dev. & Induct. Pham.* 1685 (1991). Unfortunately, this approach also has several drawbacks. First, it is difficult to find a particular polymer for each drug of interest to form a thermodynamically stable solid solution. Thermodynamic stability depends on interactions between the drug and polymer, which are generally not well understood and the number of polymers acceptable for use in oral dosage forms is quite limited. Second, thermodynamically stable dispersions of a drug and a polymer are typically only possible at low concentration of drug in the dispersion. This requires a large amount of polymer to be dosed with the drug which often makes dosing by conventional dosage form (such as pills, tablets, or capsules) impractical.

What is therefore desired is a composition comprising a dispersion of a low-solubility drug in a polymer that provides superior bioavailability, together with improved stability of the dispersion in typical storage environments, particularly for dispersions where the drug is present in concentrations above its equilibrium value.

BRIEF SUMMARY OF THE INVENTION

In a first aspect, the present invention provides a composition comprising a solid dispersion comprising a low-solubility drug and at least one of a particular class of polymers. At least a major portion of the drug in the resulting dispersion is amorphous. The dispersion is prepared by a solvent processing method. The polymer has a glass transition temperature of at least 100° C. measured at a relative humidity of 50%.

The term drug is conventional denoting a compound having beneficial, prophylactic, and/or therapeutic properties when administered to an animal, particularly a human.

Another aspect of the invention comprises the same composition except that (1) the dispersion itself is characterized by a glass transition temperature of at least 50° C. measured at a relative humidity of 50% and (2) the dispersion may be formed by any method.

In a third aspect of the invention there is provided a composition comprising a solid dispersion comprising a low-solubility drug and a stabilizing polymer. The composition also includes a concentration-enhancing polymer that increases the maximum measured concentration of the drug when exposed to an environment of use. The stabilizing polymer has a glass transition temperature that is greater than the glass transition temperature of the concentration-enhancing polymer measured at a relative humidity of 50%.

In a fourth aspect of the invention, there is provided a composition comprising a solid dispersion comprising a low-solubility drug and at least one of a particular class of cellulosic polymers. At least a major portion of the drug is amorphous. The polymer has a glass transition temperature of at least 100° C. measured at a relative humidity of 50%.

In a fifth aspect of the invention, there is provided a composition comprising a solid dispersion comprising a low-solubility drug and at least one polymer. At least a major portion of the drug once dispersed in the dispersion, is amorphous. The polymer has a glass transition temperature of at least 100° C. measured at 50% relative humidity. The dispersion is substantially homogeneous. Preferably, the dispersion exhibits a single glass transition temperature.

In a sixth aspect of the invention, a method is provided for treating a disorder by administering to a patient a drug-containing dispersion and a concentration-enhancing polymer. The dispersion comprises a low-solubility drug and at least one stabilizing polymer, the stabilizing polymer having a glass transition temperature that is greater than the glass transition temperature of the concentration-enhancing polymer. The concentration-enhancing polymer increases the maximum drug concentration in an environment of use relative to a control composition comprising an equivalent quantity of undispersed drug.

The present invention has several advantages over the prior art. A solid dispersion of a low-solubility drug and a polymer can increase bioavailability of the low-solubility drug by creating an enhanced concentration of the drug in an aqueous environment of use. The invention provides compositions that are surprisingly stable in typical storage environments compared to other solid dispersions. Accordingly, the compositions of the present invention enable the use of low-solubility drugs which otherwise do not have a high bioavailability when in crystalline form, and also enhance bioavailability to reduce the dosage of the drug. Further, the invention provides for superior bioavailability of the drug in an aqueous use environment.

The foregoing and other features and advantages of the invention will be more readily understood upon consideration of the following detailed description of the intention, taken in conjunction with the accompanying drawings.

DETAILED DESCRIPTION OF THE INVENTION

Figure 1:
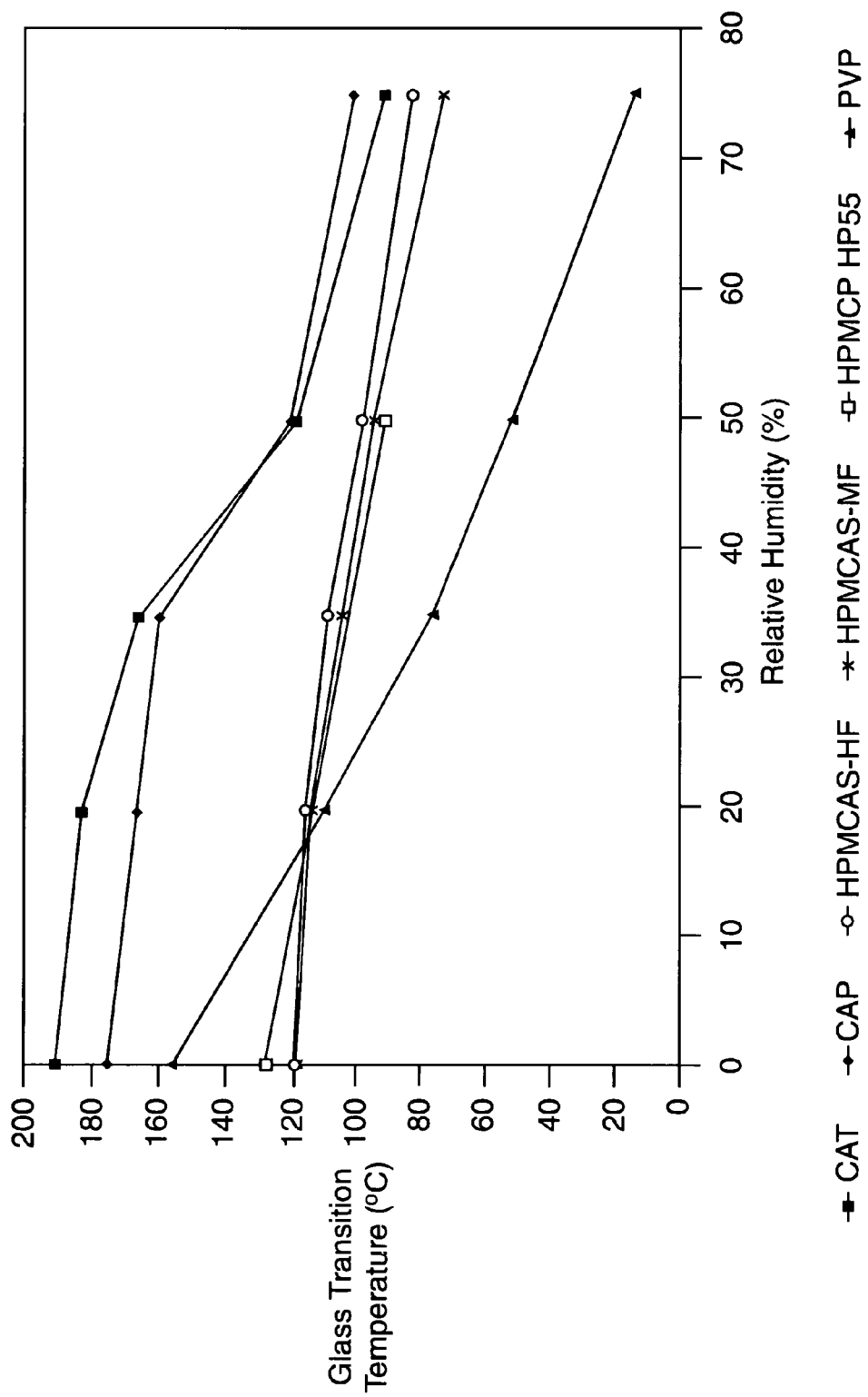
FIG. 1 is a graph showing the glass transition temperatures of several polymers as a function of relative humidity.

A first aspect of the present invention provides a composition comprising a solid dispersion comprising a low-solubility drug and at least one polymer. The solid dispersion and suitable polymer(s) and drug(s) will be discussed in more detail as follows.

Solid Dispersions

The solid dispersions of the present invention comprise a low-solubility drug and at least one polymer. At least a major portion of the drug in the dispersion is present in the amorphous, rather than the crystalline state. By "amorphous" is meant simply that the drug is in a non-crystalline state. The amorphous drug can exist as a pure drug phase, as a solid solution of drug homogeneously distributed throughout the polymer or any combination of these states or those that lie intermediate between them. As used herein, the term "a major portion" of the drug means that at least 60% of the drug once dispersed in the dispersion is in the amorphous form, rather than the crystalline form. Preferably, the drug in the dispersion is substantially amorphous. As used herein, substantially amorphous means that the amount of the drug in crystalline form does not exceed 20%. More preferably, the drug in the dispersion is "almost completely amorphous" meaning that the amount of drug in the crystalline form does not exceed 10% as measured by powder X-ray diffraction or differential scanning calorimetric ("DSC"), or any other standard quantitative measurement.

Generally speaking, a solid dispersion is not physically stable and the amorphous drug present in the dispersion tends to recrystallize over time. This is especially true where the concentration of the drug in the polymer is greater than its equilibrium value or supersaturated. Such dispersions may be considered a supersaturated solid solution. Such supersaturated solid solutions are not thermodynamically stable. Over time it is believed that such solid dispersions will separate into a mixture of two or more phases, one phase enriched in drug and the other phase enriched in polymer. The drug-rich phase generally contains crystalline or amorphous drug and the other phase generally contains a solid solution of the drug and polymer in which the drug is at a lower concentration (than the drug-rich phase) and may be at or near equilibrium concentration in the polymer. Drug within the drug-rich phase may be crystalline or amorphous. Further, over time, the amorphous drug within the drug-rich phase that has separated from the polymer may also tend to crystallize. Separation of a drug-rich phase generally results in a decrease in bioavailability, because the bioavailability of the amorphous or crystalline form of a low-solubility drug is usually much less than its bioavailability in an amorphous drug dispersion in polymer. Thus, over time, the bioavailability of the drug in solid dispersions tends to decrease as increasing amounts of the drug separate as amorphous or crystalline drug.

However, it has been determined that dispersions can be made that are physically stable over a relatively long period of time, i.e., up to several months or even years. Surprisingly, it has been found that the stability of the dispersion is related to the glass transition temperature ("$T_g$") of the dispersion and the degree of homogeneity of the dispersion. As used herein, the change in "stability" refers to the rate of change in the drug from a dispersed amorphous state to a state in which drug exists as a drug-rich amorphous or crystalline state over time in a typical storage environment. Such a change generally, in turn, decreases the bioavailability of the drug when dosed to a mammal. It has been found in many cases that the rate of change of the drug from the dispersed amorphous state to the crystalline state in the dispersion decreases with increasing $T_g$ of the dispersion (e.g., the dispersion has improved stability). Thus, the rate at which the amorphous drug in the dispersion crystallizes can be reduced by increasing the dispersion's $T_g$. This is unexpected, since the conventional approach to stabilizing drug and polymer dispersions has been to find particular drug/polymer pairs that form thermodynamically stable dispersions.

Directly contrary to conventional approaches of attempting to find thermodynamically stable dispersions, it has been determined that solid dispersions can be made which are essentially kinetically stable, even though they may not be thermodynamically stable. While not wishing to be bound by any particular theory, it is believed that the $T_g$ of an amorphous material is related to the mobility of its constituent components. Increasing a dispersion's $T_g$ may therefore inhibit the mobility of the drug within the dispersion. Thus, by increasing the $T_g$ of the solid dispersion, the mobility of the drug may be decreased and hence its ability to form relatively pure domains, be they amorphous or crystalline, may be inhibited. In cases where amorphous drug-rich domains form, the drug present in such domains generally crystallizes rapidly relative to its rate of crystallization in the original dispersion. Further, by initially creating substantially homogenous dispersions, that is, dispersions wherein the drug is not present in drug-rich domains, the drug tends to be stabilized by the polymer and is not present in relatively pure drug domains that tend to be susceptible to crystallization.

It is believed that the present invention is also applicable to relatively stable dispersions, be they kinetically or thermodynamically stable, which nevertheless contain drugs which, in a relatively pure amorphous state, would be unstable themselves. That is, the invention is applicable to drugs that in their pure amorphous state tend to be susceptible to crystallization.

By raising the dispersion's $T_g$ and uniformly dispersing the drug throughout the polymer so that the dispersion is substantially homogenous, it should be possible to prevent the formation of relatively pure amorphous drug domains and thereby stabilize the amorphous drug dispersion. Thus, the present invention finds utility in both thermodynamically stable and thermodynamically unstable dispersions.

To achieve good stability, the dispersions of the present invention should have the following features. First, the dispersion is preferably substantially homogeneous so that the amorphous drug is dispersed as homogeneously as possible throughout the polymer. As. used herein, "substantially homogeneous" means that the drug present in relatively pure amorphous domains within the solid dispersion is relatively small, on the order of less than 20%, and preferably less than 10%. While the dispersion may have some drug-rich domains, it is preferred that the dispersion itself have a single $T_g$ which demonstrates that the dispersion is substantially homogenous. This contrasts with a physical mixture of pure amorphous drug particles and pure amorphous polymer particles which generally display two distinct $T_g$s, one that of the drug and one that of the polymer. Nevertheless, since the degree of homogeneity is only one factor to consider in terms of stabilizing the drug, even dispersions which are not substantially homogenous may be stabilized by increasing the $T_g$ of the dispersion.

Second, the dispersion's $T_g$ should be relatively high. Because water is present under most practical storage conditions, the solid drug dispersion must be stable even in the presence of moderate humidity (relative humidity on the order of 50 to 70%). The polymer(s) and drug content (wt % of drug that makes up the dispersion) should be chosen such that the $T_g$ of the resulting dispersion, when equilibrated with humid air having a relative humidity ("RH") of about 50%, is at least 30° C. (i.e., a typical storage environment), and preferably greater than 50° C. As used herein, relative humidity is given as the partial pressure of water in the storage atmosphere (typically air) divided by the partial pressure of pure water at the storage temperature times 100%. In cases where two (or more) $T_g$s are observed, the lowest glass transition temperature of the resulting dispersion when equilibrated with humid air with an RH of about 50% is at least 30° C., and preferably 50° C. It should be noted here that the mobility of a material varies greatly as a function of temperature, particularly at temperatures near the $T_g$ of the material. (See for example, C. M. Roland and K. L. Ngal (104 J. Chem. Phys. 2967-2970 (1996)) and R. Bohmer, et al. (99 J. Chem. Phys. 4201-4209 (1992)) which discuss the "fragility" of glasses.) Fragility is essentially a measure of the slope of the log of the average relaxation time of a glassy material (tau) versus temperature near the $T_g$ of the glass. The fragility of glasses of the type we are considering here can be sufficiently high that tau, which is roughly proportional to mobility, can increape by from 5-fold to 20-fold for every 10° C. increase in temperature. Thus, for example, for glassy materials at temperatures just below their $T_g$, mobility may increase 10-fold for every 10° K temperature rise. Thus, raising the $T_g$ of a material even 5 or 10° C. can substantially increase the stability of the material.

$T_g$ as used herein is the characteristic temperature where a glassy material, upon gradual heating, undergoes a relatively rapid (e.g., 10 to 100 seconds) physical change from a glass state to a rubber state. The glass-transition region is generally the temperature region where the structural relaxation time of a material in the glass state falls in the range of a few seconds to tens of minutes so that relaxation can be measured over a convenient time period. Specifically, Moynihan, et al. (279 Ann. N.Y. Acad. Sci. 15-35 (1976)) have stated that the widely accepted average relaxation time (tau) for a material at this $T_g$ is approximately 100 seconds. As we describe below, scientists have developed several techniques for measuring the $T_g$ of a glass material that are consistent with this definition. In the case of polymers, there are typically several physical changes that occur upon heating. Each of these changes corresponds to an increase in the mobility of the polymer. These transitions are designated α, β, γ, where α signifies the highest temperature event, β the next highest and γ the next. $T_g$ as used herein, refers to the α-transitions. At this temperature region there is a discontinuous change in several important material properties, such as specific heat, mechanical modulus, relaxation rate, long-range molecular mobility, and the change in volume with temperature.

Many factors influence a polymer's $T_g$, the most important of which are the chemical structure and molecular weight. In general, organic materials that have some combination of high levels of hydrogen bonding, polar interactions and n-electron interactions, rigid polymer backbones and high molecular weights give rise to higher $T_g$ values.

The $T_g$ of an amorphous material such as a polymer, drug or dispersion can be measured by several techniques, including by a dynamic mechanical analyzer (DMA), a dilatometer, dielectric analyzer, and by a differential scanning calorimeter (DSC). The exact values measured by each technique can vary somewhat but usually fall within 100 to 30° C. of each other. The reason for the variation is the nature of the measurement. Fort example, DMA measures the mechanical response (elastic and inelastic) to an oscillating mechanical stress. In comparison, DSC measures the total heat flow into and out of the sample as a function of temperature. In both cases a glass transition is seen, but as a rule, the $T_g$ seen in the DMA measurement occurs at a higher temperature (typically 10-20° C.) as compared to one measured by DSC. This is due to the fact that the DSC experiment measures the heat flow needed for breaking intermolecular bonds and increasing the number of conformational states that are populated, while DMA measures how the bulk mechanical properties change as a result of the microscopic changes, which necessarily occurs at a higher temperature.

It should be noted that the $T_g$ for a homogeneous blend of two amorphous materials can be estimated where the densities of the two components are similar, as is roughly the case for many drugs and polymers. The following expression, called the Gordon-Taylor Equation (M. Gordon and J. S. Taylor, 2 J. of Applied Chem. 493-500 (1952)) approximates $T_{g,1,2}$ of a two-component mixture:

$$T_{g,1,2} = \frac{w_1 T_{g1} + K w_2 T_{g2}}{w_1 + K w_2}$$

Where $w_1$ and $w_2$ are the weight fractions of the components 1 and 2, $T_{g1}$ and $T_{g2}$ are the glass transition temperatures of components and 2 (in degrees Kelvin), respectively, $T_{g,1,2}$ is the glass transition temperature of the mixture of components 1 and 2, and K is a constant related to the free volumes of the two compounds.

Corresponding expressions can be written for a mixture of a larger number of components. It follows from these expressions (and the fact that the $T_g$ of many amorphous drugs is quite low) that in order for the $T_g$ of a dispersion to meet the stability criteria mentioned previously ($T_g$>30° C. at 50% RH; preferably $T_g$>50° C. at 50% RH) that, first, a significant portion of the dispersion should comprise a polymer having a relatively high $T_g$. Second, the equilibrium water content (water has an amorphous $T_g$ of about 135-138° K) should be low. Third, the drug content of the dispersion should not be too high. This is particularly true if the amorphous drug itself has a low $T_g$ in the presence of humid air. The amounts of the various components of the dispersion accordingly will be chosen such that the resulting glass transition temperature of the dispersion is greater than 30° C. measured at 50% RH and preferably greater than 50° C. measured at 50% relative humidity.

Thus, the $T_g$ of a drug dispersion can be made high and, therefore, the stability of the dispersion increased by keeping the drug content low and the polymer content high. In a relative sense, this is true even of dispersions made from polymers with $T_g$'s sufficiently low that they are outside the invention. Thus, a dispersion of a drug in a polymer such as HPMCP, which has a $T_g$ at 50% RH of about 90° C. can have a $T_g$ greater than 50C, as long as the drug content is low (e.g., on the order of about 10 to 20 wt % or less). Despite the fact that stable dispersions may be made by homogeneously dispersing the drug at a low concentration in a known, moderate $T_g$ polymer, such dispersions are often impractical for use in a conventional dosage form such as a tablet due to the large amount of dispersion required. Thus, for example, a drug with a therapeutic dose of 100 mg would require 1000 mg of a 10 wt % drug dispersion making it impractical for incorporation into a single oral dosage form such as a tablet. In contrast to this, a dispersion of the same drug in a high $T_g$ polymer of the invention, could have a much higher drug loading (e.g., 20 to 30%) and still have a high enough $T_g$ for good stability ($T_g$>30° C. or preferably $T_g$>50° C.).

Because the glass transition is a kinetic process, the time scale for the measurement of $T_g$ also has an effect on the measured $T_g$. For calorimetric experiments, the glass transition temperature is dependent on the scanning rate of the calorimeter-occurring at higher temperature for faster scan rates. As used herein when referring to numerical values for the $T_g$ of a material, the $T_g$ of a material is the highest α-transition measured using DSC at a 10° C./min. scan rate and for which the material has been preequillibrated with a specific RH. In addition, to minimize the loss of absorbed water during the DSC experiment, the sample should, following equilibration of the appropriate RH, be sealed in a vapor-tight sample holder, such as a Perkin Elmer 30 μL, 2-atm aluminum autosampler DSC pan.

Stability of the dispersion over time may be measured in a variety of ways. First, the change in the Maximum Drug Concentration ("MDC") which results when the dispersion is dissolved in an appropriate in vitro test solution, such as a Model Fasted Duodenal ("MFD") solution may be measured. This MDC measured in vitro has been shown to be related to the bioavailability of the dispersion in vivo. In addition, the change in the Area Under the Curve ("AUC"), which is the integration of a plot of the drug concentration versus time, may also be measured. AUC's can be determined for in vitro dissolution tests by plotting the drug concentration in the test solution over time or for in vivo tests by plotting the drug concentration in the patient's blood over time. AUC's are well understood, frequently used tools in the pharmaceutical arts and have been extensively described, for example, in Welling, "*Pharmacokinetics Processes and Mathematics*," ACS Monograph 185 (1986). In addition, stability may be determined by evaluating the change in the physical state (crystalline vis-a-vis amorphous) of the drug in the dispersion. Specifically, the fraction of drug in the crystalline state in the dispersion may be measured by any standard physical measurement, such as X-ray diffraction or Scanning Electron Microscope ("SEM") analysis.

In a preferred embodiment, the composition comprising the solid dispersion provides enhanced bioavailability of the drug. It has been determined that in vitro dissolution of a dispersion in MFD solution is a good indicator of in vivo performance and bioavailability. In particular, a dispersion can be dissolution-tested by adding it to MFD solution and agitating to promote dissolution. Preferably, the dispersion of the present invention provides an MDC of the drug by a factor of at least 1.5 relative to the equilibrium concentration of a control composition comprising an equivalent quantity of undispersed drug. The comparison composition is conventionally the undispersed drug alone (e.g., typically, the crystalline drug alone in its most thermodynamically stable crystalline form, or in cases where a crystalline form of the drug is unknown, the control may be the amorphous drug alone) or the undispersed drug plus a weight of inert diluent equivalent to the weight of polymer in the test composition. More preferably, the MDC of drug achieved with the solid dispersions of the present invention exceeds the equilibrium drug concentration of the control by a factor of at least three, and more preferably by a factor of at least five.

Alternatively, the dispersion of the present invention provides an AUC, for dissolution times between 0 and 90 to 1200 minutes, in an in vitro dissolution test that is 1.25-fold higher than that of a control composition comprising an equivalent quantity of undispersed drug.

Alternatively, the dispersion of the present invention, when dosed orally to a human or other animal, provides an AUC in drug concentration in the blood that is 1.25-fold higher than that observed when a control composition comprising an equivalent quantity of undispersed drug is dosed.

A typical test to evaluate enhanced bioavailability can be conducted by (1) dissolving a sufficient quantity of control composition, typically the drug alone, in the in vitro test medium, typically MFD solution, to achieve equilibrium concentration of drug; (2) dissolving a sufficient quantity of dispersion, in an equivalent test medium, such that if all the drug dissolved, the theoretical concentration would exceed the equilibrium concentration of the undispersed drug by a factor of at least 2; and (3) determining whether the measured MDC of the dispersion in the test medium is at least 1.5-fold that of the equilibrium concentration of the undispersed drug. The concentration of dissolved drug is typically measured as a function of time by sampling the drug and plotting concentration vs. time so that the MDC can be ascertained. To avoid drug particulates which would give an erroneous determination, the test solution is either filtered or centrifuged. "Dissolved drug" is typically taken as that material that either passes a 0.45 μm syringe filter or, alternatively, the material that remains in the supernatant following centrifugation. Filtration can be conducted using a. 13 mm, 0.45 μm polyvinylidine difluoride syringe filter sold by Scientific Resources under the trademark TITAN®. Centrifugation is typically carried out in a polypropylene microcentrifuge tube by centrifuging at 13,000 G for 60 seconds. Other similar filtration or centrifugation methods can be employed and useful results obtained. For example, using other types of microfilters may yield values somewhat higher or lower (±10-40%) than that obtained with the filter specified above but will still allow identification of preferred dispersions. It is recognized that this definition of "dissolved drug" encompasses not only monomeric solvated drug molecules but also a wide range of species such as polymer/drug assemblies that have submicron dimensions such as drug aggregates, aggregates of mixtures of polymer and drug, micelles, polymeric micelles, colloidal particles or nanocrystals, polymer/drug complexes, and other such drug-containing species that are present in the filtrate or supernatant in the specified dissolution test.

Bioavailability of drugs in the dispersions of the present invention can also be tested in vivo in animals or humans using conventional methods for making such a determination. An in vivo test, such as a crossover study, may be used to determine whether a dispersion provides an enhanced drug concentration in the blood (serum or plasma) versus time area under the curve (AUC) for a test subject, dosed with the dispersion relative to the drug concentration in the blood versus time AUC for a test subject dosed with a control composition as described above. In an in vivo crossover study a "test dispersion composition" is dosed to half a group of 12 or more humans and, after an appropriate washout period (e.g., one week) the same subjects are dosed with a "control composition" that comprises an equivalent quantity of undispersed drug as the "test dispersion composition." The other half of the group is dosed with the control composition first, followed by the test dispersion composition. The bioavailability is measured as the area under the curve (AUC) determined for each group. In vivo determinations of AUC can be made by plotting the serum or plasma concentration of drug along the ordinate (y-axis) against time along the abscissa (x-axis). Generally, the values for AUC represent a number of values taken from all of the subjects in a patient test population and are, therefore, mean values averaged over the entire test population. By measuring the AUC for a population to which the test dispersion composition has been administered and comparing it with the AUC for the same population to which the control composition has been administered, the test dispersion composition can be evaluated. The determination of AUCs is a well-known procedure and is described, for example, in the same Welling ACS Monograph mentioned above.

The Dispersion Polymer(s)

Polymers which are suitable for use in the dispersions of the present invention are selected to provide a $T_g$ for the dispersion as described above. The polymer should have at least some solubility in aqueous solution at physiologically relevant pHs (e.g. pH 1-8). Virtually any such polymer which is inert should be suitable. By "inert" is merely meant not undesirably-reactive or bioactive, yet still capable of positively affecting the drug's bioavailablity. The polymer also should be biologically inert or non-toxic in the sense that it is acceptable for oral administration to a mammal such as a human. The amount of the polymer present in the dispersion may range from about 20 wt % to about 99 wt % of the dispersion. A preferred class of polymers is cellulosic polymers and esters and ethers thereof, as well as mixed esters and ethers, including both so-called "enteric" and "non-enteric" polymers.

As discussed above, the $T_g$ of the polymer should be great enough so that the resulting dispersion has a relatively high $T_g$ (greater than 30° C. at 50% RH). Although polymers which have a $T_g$ when dry (e.g., a moisture content equivalent to an RH of about 10% or less) that is greater than 140° C. may provide good stability for solid dispersions if protected from moisture, they often become unstable when exposed to ambient moisture levels (e.g., an RH of 30% to 90%). Thus, since the dispersion may be stored in conditions subject to relative humidity in excess of 50%, it is necessary to select polymers having relatively high $T_g$'s at high relative humidity. Some polymers exhibit marked decreases in $T_g$ with increasing water content due to the absorption of water. FIG. 1 shows the $T_g$ values measured as a function of relative humidity for six different polymers. As is shown in FIG. 1, the $T_g$ of polyvinyl pyrrolidone (PVP) drops much more rapidly with increasing RH than the $T_g$ for the other polymers. This is because the amount of water absorbed by PVP at a given RH is much larger than for the other polymers. Preferably, the polymer does not absorb more than 10% by weight of water at 50% RH. In any event, the $T_g$ of the polymer should remain relatively high when equilibrated with humid air (50% RH). In a preferred embodiment of the invention, the polymer should have a $T_g$ of at least 100° C. at 50% RH, and preferably should be at least 105° C. at 50% RH, and even more preferably should be at least 110° C. at 50% RH. As mentioned previously, stability can be dramatically improved by increasing $T_g$ by even small amounts of 5 to 10° C. Polymers within the scope of the present invention include cellulose acetate phthalate (CAP) and cellulose acetate trimellitate (CAT).

It should be noted that a polymer name such as "cellulose acetate phthalate" refers to any of the family of cellulosic polymers that have acetate and phthalate groups attached via ester linkages to a significant fraction of the cellulosic polymer's hydroxyl groups. Generally, the degree of substitution of each substituent group can range from 0.2 to 2.8 as long as the other criteria of the polymer are met. "Degree of substitution" refers to the average number of the three hydroxyls per saccharide repeat unit on the cellulose chain that have been substituted. For example, if all of the hydroxyls on the cellulose have been phthalate substituted, the phthalate-degree of substitution is 3. Also included within each polymer family type are cellulosic polymers that have additional substituents added in relatively small amounts that do not substantially alter the performance of the polymer.

More generally, one class of polymers which meets the requirements of the present invention includes cellulosic polymers with an ester- or ether-linked aromatic substituent in which the polymer has a degree of substitution of at least 0.2. Cellulosics with a significant fraction of aromatic substituents generally have the high $T_g$ values and low water absorption values desirable for utility in the present invention. Exemplary aromatic substituents include benzoate, phenoxy and ethoxy phenyl. For such aromatic-substituted polymers to also have the requisite aqueous solubility, it is also desirable that sufficient hydrophilic groups such as hydroxypropyl or carboxylic acid functional groups be attached to the polymer. Such carboxylic acid groups can be ether-linked to the polymer as is the case for carboxy ethyl groups, or they may be attached via ester linkages such as for succinate groups. A class of substituents that is particularly desirable is that comprising carboxylic acid functional aromatic substituents, as they provide both an aromatic group to promote a high $T_g$ and an ionizable carboxylic acid group that can promote aqueous solubility. Carboxylic acid-substituted aromatic groups may be attached to the cellulosic polymer via ester or ether linkages via the hydroxyl groups of the cellulose backbone or through the hydroxyl groups of other substituents such as hydroxypropoxy. Exemplary carboxylic acid-substituted aromatic groups that maybe attached via ester linkages include phthalate, trimellilate, the various isomers of pyridinedicarboxylic acid, terephthalate, isophthalate and alkyl-substituted derivatives of these groups. Exemplary carboxylic acid-substituted aromatic groups that may be attached via ether linkages include salicylic acid, alkoxybenzoic acids such as ethoxy benzoic acid or propoxybenzoic acid, the various isomers of alkoxyphthalic acid such as ethoxyphthalic acid and ethoxyisophthalic acid, the various isomers of alkoxynicotinic acid such as ethoxynicotinic acid, and the various isomers of alkoxypicolinic acid such as ethoxypicolinic acid.

It may also be desirable to add other substituents to the polymer to obtain the desired physical properties. Exemplary ester substituents are lower carboxylic acid residues such as acetate, propionate, and butyrate; $C_1$ to $C_4$ alkoxy groups such as methoxy, ethoxy, propoxy and butoxy and $C_1$ to $C_4$ hydroxyalkoxys such as hydroxyethoxy, hydroxypropoxy and hydroxybutoxy.

A particularly desirable subset of these cellulosic polymers are those that possess both a carboxylic acid functional aromatic substituent and an alkylate substituent. Exemplary polymers include: cellulose acetate phthalate, methyl cellulose acetate phthalate, ethyl cellulose acetate phthalate, hydroxypropyl cellulose acetate phthalate, hydroxypropyl methyl cellulose acetate phthalate, hydroxypropyl cellulose acetate phthalate succinate, cellulose propionate phthalate, hydroxypropyl cellulose butyrate phthalate, cellulose acetate trimellitate, methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate-pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, and ethyl picolinic acid cellulose acetate.

Even more preferred are those cellulosics with both ester-linked phthalate or trimellitate groups and an alkylate group. Exemplary polymers of this class include: cellulose acetate phthalate, methyl cellulose acetate phthalate, hydroxypropyl cellulose acetate phthalate, hydroxypropyl methyl cellulose acetate phthalate, hydroxypropyl cellulose acetate phthalate succinate, cellulose propionate phthalate, hydroxypropyl cellulose butyrate phthalate, hydroxypropyl methyl cellulose trimellitate, cellulose acetate trimellitate, cellulose propionate trimellitate, cellulose butyrate trimellitate, cellulose acetate terephthalate, and cellulose acetate isophthalate.

Most preferred polymers are cellulose acetate phthalate, methyl cellulose acetate phthalate, hydroxypropyl cellulose acetate phthalate, cellulose acetate terephthalate, cellulose acetate isophthalate, and cellulose acetate trimellitate.

It should be noted that in the above polymer nomenclature, ether-linked substituents are recited prior to "cellulose" as the moeity attached to the ether group (e.g., "ethylbenzoic acid cellulose" has ethoxybenzoic acid substituents) and ester-linked substituents are recited after "cellulose" as the carboxylate (e.g., "cellulose phthalate" has one carboxylic acid of each phthalate moiety ester-linked to the polymer and the other carboxylic acid unreacted). However, for all of the polymers listed above, the type and degree of substitution of the substituents must be such that the $T_g$ of the resulting polymer meets the criterion listed above (e.g., $T_g$ at 50% RH is $\geq$100° C.).

In contrast, carboxylic acid functional group-substituted cellulosic polymers that do not meet this criterion are certain grades of hydroxypropyl methyl cellulose phthalate (HPMCP). In particular, HPMCP-HP50, HPMCP-HP55 and HPMCP-HP55S all absorb sufficient water upon equilibration at 50% RH that their respective $T_g$s drop below 100° C. FIG. 1 shows $T_g$ as a function of relative humidity for the polymers PVP, hydroxypropyl methyl cellulose acetate succinate (HPMCAS), and hydroxypropyl methyl cellulose phthalate (HPMCP), all polymers not included within the scope of the invention when used alone. FIG. 1 also shows the $T_g$ of CAP and CAT, both preferred embodiments of polymers suitable for use alone in the invention. As FIG. 1 shows, at high RH (e.g., 30% to 75%), the $T_g$ of CAP and CAT are much higher than the $T_g$s of the other respective polymers.

While specific polymers have been discussed as being suitable for use alone in the dispersions of the present invention, blends of polymers may also be suitable. Thus, blends of different polymers may be used to form the dispersions of the present invention, with some polymers having higher $T_g$ and others lower, so long as the resulting dispersion meets the criteria discussed above. In general, this may be achieved by including a sufficient quantity of polymer having a $T_g$ in excess of 100° C. at 50% RH.

In addition to having a high $T_g$ as described above, polymers that are preferred are those that are insoluble in gastric pH, or pH of about 1-2, but are soluble in intestinal pH, or pH of about 6-8. This should result in a dispersion which generally does not dissolve until reaching the duodenum of the intestinal tract.

The Drug

The drug in its pure state may be crystalline or amorphous, but at least a major portion of the drug is amorphous when dispersed in the solid dispersion. Preferably, the drug is in a substantially amorphous or non-crystalline state as described above. The dispersion may contain from about 1 to about 80 wt % drug, depending on the dose of the drug. In general, bioavailability and physical stability is maximized at low drug loadings (less than 10 wt % drug,in the dispersion). However, due to the practical limit of the dosage form size, higher drug loadings are often preferred and perform well.

A specific advantage of using the high $T_g$ polymers of the invention as the dispersion polymer is that they allow higher drug loadings in the dispersion to be used while still achieving a given target dispersion $T_g$ and a target level of stability. As mentioned previously the $T_g$ of a dispersion is generally dictated by the $T_g$ and the weight fraction of the components that make up the dispersion. Thus, for a given drug, and relative humidity, the higher the $T_g$ of the dispersion polymer, the higher the weight fraction (drug loading) of drug which can be used and still have a sufficiently high $T_g$ (for example, 50° C. at 50% RH) and also still have acceptable stability. For example, for a moderate $T_g$ polymer like HPMCP, the dispersion $T_g$ may drop below a value of 50° C. at 50% RH at any drug loading above about 10 wt % while for a high $T_g$ polymer like CAP, the dispersion $T_g$ may drop below a value of 50° C. at 50% RH only at drug loadings above 35 wt %.

The drug has sufficiently low aqueous solubility that it is desirable to increase its solubility either within the dosage form to improve its release characteristics or outside the dosage form to improve its concentration. Therefore, anytime one finds it desirable to raise the concentration of the drug in a use environment, the invention will find utility. The drug is a "low-solubility drug," meaning that the drug may be either "substantially water-insoluble" (which means that the drug has a minimum aqueous solubility at, physiologically relevant pH (e.g., pH 1-8) of less than 0.01 mg/mL), "sparingly water-soluble," that is, has a water solubility up to about 1 to 2 mg/mL, or even low to moderate water-solubility, having a water-solubility as high as about 20 to 40 mg/mL. In general, it may be said that the drug has a dose-to-aqueous solubility ratio greater than 100 mL, where the drug solubility is the minimum value observed in any physiologically relevant aqueous solution (e.g., those with pH values between 1 and 8) including USP simulated gastric and intestinal buffers. In some cases, it is also desirable to enhance the solubility of the drug within the dosage form to increase the rate of diffusion or release from the dosage form or to improve the absorption of drug in the colon. In such cases, the invention may be applied to drugs with solubility as high as 20 to 40 mg/mL. This is particularly true when it is desired to deliver a solution of the drug. In such cases, the dose-to-aqueous solubility ratio may be as low as 1 to 100 mL.

Virtually any beneficial therapeutic agent that meets the solubility criteria may be used as the drug in the present invention. In addition, the drug may be employed in the form of its pharmaceutically acceptable salts as well as in anhydrous and hydrated forms.

Preferred classes of drugs include, but are not limited to, antihypertensives, antianxiety agents, anticlotting agents, anticonvulsants, blood glucose-lowering agents, decongestants, antihistamines, antitussives, antineoplastics, beta blockers, anti-inflammatories, antipsychotic agents, cognitive enhancers, cholesterol-reducing agents, antiobesity agents, autoimmune disorder agents, anti-impotence agents, antibacterial and antifungal agents, hypnotic agents, anti-Parkinsonism agents, anti-Alzheimer's disease agents, antibiotics, anti-depressants, and antiviral agents.

Specific examples of the above and other classes of drugs and therapeutic agents deliverable by the invention are set forth below, by way of example only. For each named drug, it should be understood that included are the neutral form of the drug, pharmaceutically acceptable salts, as well as prodrugs. Specific examples of antihypertensives include prazosin, nifedipine, trimazosin and doxazosin; a specific example of an antianxiety agent is hydroxyzine; a specific example of a blood glucose-lowering agent is glipizide; a specific example of an anti-impotence agent is sildenafil citrate; specific examples of antineoplastics include chlorambucil, lomustine and echinomycin; a specific example of an imidazole-type antineoplastic is tubulazole; specific examples of antiinflammatory agents include betamethasone, prednisolone, aspirin, flurbiprofen and (+)-N-{4-[3-(4-fluorophenoxy)phenoxy]-2-cyclopenten-1-yl}-N-hyroxyurea; a specific example of a barbiturate is phenobarbital; specific examples of antivirals include acyclovir and virazole; specific examples of vitamins/nutritional agents include retinol and vitamin E; specific examples of beta blockers include timolol and nadolol; a specific example of an emetic is apomorphine; specific examples of a diuretic include chlorthalidone and spironolactone; a specific example of a an anticoagulant is dicumarol; specific examples of cardiotonics include digoxin and digitoxin; specific examples of androgens include 17-methyltestosterone and testosterone; a specific example of a mineral corticoid is desoxycorticosterone; a specific example of a steroidal hypnotic/anesthetic is alfaxalone; specific examples of anabolic agents include fluoxymesterone and methanstenolone; specific examples of antidepression agents include sulpiride, [3,6-dimethyl-2-(2,4,6-trimethyl-phenoxy)-pyridin-4-yl]-(1-ethylpropyl)-amine, 3,5-dimethyl-4-(3'-pentoxy)-2-(2',4',6'-trimethylphenoxy)pyridine, paroxetine, fluoxetine, venlafaxine and sertraline; specific examples of antibiotics include ampicillin and penicillin G; specific examples of anti-infectives include benzalkonium chloride and chlorhexidine; specific examples of coronary vasodilators include nitroglycerin and mioflazine; a specific example of a hypnotic is etomidate; specific examples of carbonic anhydrase inhibitors include acetazolamide and chlorzolamide; specific examples of antifungals include econazole, terconazole and griseofulvin; a specific example of an antiprotozoal is metronidazole; specific examples of anthelmintic agents include thiabendazole and oxfendazole; specific examples of antihistamines include astemizole, levocabastine, cetirizine, and cinnarizine; specific examples of antipsychotics include ziprasidone, fluspirilene and penfluridole; specific examples of gastrointestinal agents include loperamide and cisapride; specific examples of serotonin antagonists include ketanserin and mianserin; a specific example of an anesthetic is lidocaine; a specific example of a hypoglycemic agent is acetohexamide; a specific example of an anti-emetic is dimenhydrinate; a specific example of an antibacterial is cotrimoxazole; a specific example of a dopaminergic agent is L-DOPA; specific examples of anti-Alzheimer's Disease agents are THA and donepezil; a specific example of an anti-ulcer agent/H2 antagonist is famotidine; specific examples of sedative/hypnotic agents include chlordiazepoxide and triazolam; a specific example of a vasodilator is alprostadil; a specific example of a platelet inhibitor is prostacyclin; specific examples of ACE inhibitor/antihypertensive agents include enaprilic acid and lisinopril; specific examples of tetracycline antibiotics include oxytetracycline and minocycline; specific examples of macrolide antibiotics include erythromycin, azithromycin, clarithromycin, and spriamycin; specific examples of glycogen phosphorylase inhibitors include [R-(R*S)]-5-chloro-N-[2-hydroxy-3-[methoxymethylamino]-3-oxo-1-(phenylmethyl)propyl]propyl]-1H-indole-2-carboxamide and 5-chloro-1H-indole-2-carboxylic acid [(1S)-benzl;-3((3R, 4S)-dihydroxypyrrolidin-1-yl-)-(2R)-hydroxy-3-oxypropyl] amide.

Further examples of drugs deliverable by the invention are the glucose-lowering drug chlorpropamide, the anti-fungal fluconazole, the anti-hypercholesterolemic atorvastatin calcium, the antipsychotic thiothixene hydrochloride, the anxiolytics hydroxyzine hydrochloride and doxepin hydrochloride, the anti-hypertensive amlodipine besylate, the anti-inflammatories piroxicam and celicoxib, and the antibiotics carbenicillin indanyl sodium, bacampicillin hydrochloride, troleandomycin, and doxycycline hyclate.

Further examples of drugs deliverable by the invention include: an antidepression drug, [3,6-Dimethyl-2-(2,4,6-trimethyl-phenoxy)-pyridin-4-yl]-(1-ethyl-propyl)-amine

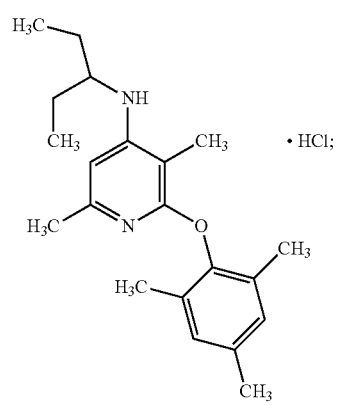 [SMILES: CCC(CC)Nc1cc(C)nc(Oc2c(C)cc(C)cc2C)c1C ; "· HCl;"]

and [3,6-Dimethyl-2-(2,4,6-trimethyl-phenoxy)-pyridin-4-yl]-(1-ethyl-propyl)-amine hydrogen chloride

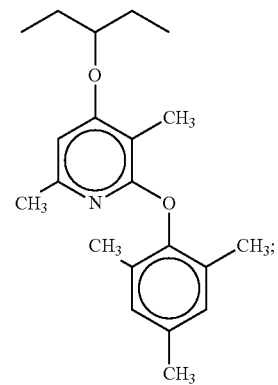

a glycogen phosphorylase inhibitor, 5-chloro-1H-indole-2-carboxylic acid [(1S)-benzyl-3-((3R,4S)-dihydroxypyrrolidin-1-yl-)-(2R)-hydroxy-3-oxypropyl]amide

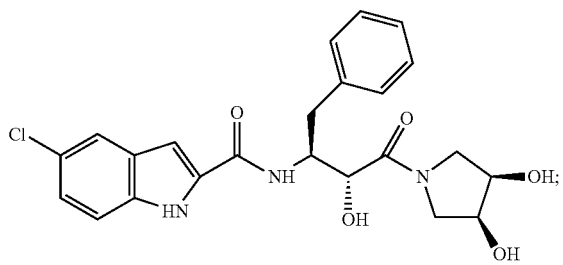 [SMILES: O=C(N[C@@H](Cc1ccccc1)[C@@H](O)C(=O)N1C[C@@H](O)[C@@H](O)C1)c1cc2cc(Cl)ccc2[nH]1]

a glycogen phosphorylase inhibitor, [R-(R*,S*)]-5-chloro-N-[2-hydroxy-3-[methoxymethylamino]-3-oxo-1-(phenylmethyl)propyl]-1H-indole-2-carboxamide

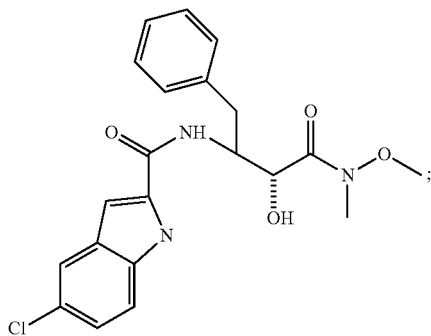 [SMILES: CON(C)C(=O)[C@H](O)C(Cc1ccccc1)NC(=O)c1cc2cc(Cl)ccc2[nH]1 ; ";"]

an antidepression drug, 3,6-dimethyl-4-(3'-pentoxy)-2-(2',4'6'-trimethylphenoxy)pryridine

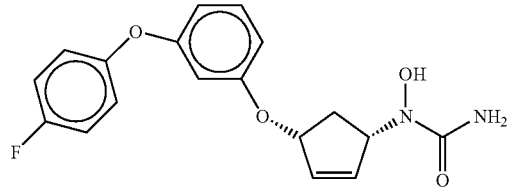

and an antiinflammatory, (+)-N-{4-[3-(4-Fluorophenoxy)phenoxy]-2-cyclopenten-1-yl}-N-hydroxyurea.

Method of Making Dispersions

The dispersions of the present invention may be made according to any known process which results in at least a majority (at least 60%) of the drug being in the amorphous state. Exemplary mechanical processes include milling and extrusion; melt processes include high temperature fusion and solvent modified fusion; and solvent processes include non-solvent precipitation, spray coating and spray-drying. Although the dispersions of the present invention may be made by any of these processes, the dispersions generally have their maximum bioavailability and stability when the drug is dispersed in the polymer such that it is substantially amorphous and substantially homogeneously distributed throughout the polymer. Although in some cases such substantially amorphous and substantially homogeneous dispersions may be made by any of these methods, it has been found that such dispersions are preferably formed by "solvent processing," which consists of dissolution of the drug and one or more polymers in a common solvent. "Common" here means that the solvent, which can be a mixture of compounds, will simultaneously dissolve the drug and the polymer(s). After both the drug and the polymer have been dissolved, the solvent is rapidly removed by evaporation or by mixing with a non-solvent. Exemplary processes are spray-drying, spray-coating (pan-coating, fluidized bed coating, etc.), and precipitation by rapid mixing of the polymer and drug solution with $CO_2$, water, or some other non-solvent. Preferably, removal of the solvent results in a solid dispersion which is a solid solution of drug dispersed in the polymer(s). When the resulting dispersion constitutes a solid solution of drug in polymer, the dispersion may be thermodynamically stable, meaning that the concentration of drug in the polymer is at or below its equilibrium value, or it may be considered a supersaturated solid solution where the drug concentration in the dispersion polymer(s) is above its equilibrium value.

The solvent may be removed through the process of spray-drying. The term spray-drying is used conventionally and broadly refers to processes involving breaking up liquid mixtures into small droplets (atomization) and rapidly removing solvent from the mixture in a container (spray-drying apparatus) where there is a strong driving force for evaporation of solvent from the droplets. The strong driving force for solvent evaporation is generally provided by maintaining the partial pressure of solvent in the spray-drying apparatus well below the vapor pressure of the solvent at the temperature of the drying droplets. This is accomplished by either (1) maintaining the pressure in the spray-drying apparatus at a partial vacuum (e.g., 0.01 to 0.50 atm); (2) mixing the liquid droplets with a warm drying gas; or (3) both.

Essentially, solvents suitable for spray-drying can be any organic compound in which the drug and polymer are mutually soluble. Preferably, the solvent is also volatile with a boiling point of 150° C. or less. In addition, the solvent should have relatively low toxicity and be removed from the dispersion to a level that is acceptable according to The International Committee on Harmonization (ICH) guidelines. Removal of solvent to this level may require a processing step such as tray-drying subsequent to the spray-drying or spray-coating process. Preferred solvents include alcohols such as methanol, ethanol, n-propanol, iso-propanol, and butanol; ketones such as acetone, methyl ethyl ketone and methyl iso-butyl ketone; esters such as ethyl acetate and propylacetate; and various other solvents such as acetonitrile, methylene chloride, toluene, and 1,1,1-trichloroethane. Lower volatility solvents such as dimethyl acetamide or dimethylsulfoxide can also be used. Mixtures of solvents, such as 50% methanol and 50% acetone, can also be used, as can mixtures with water as long as the polymer and drug are sufficiently soluble to make the spray-drying process practicable. Generally, non-aqueous solvents are preferred meaning that the solvent comprises less than about 40 wt % water.

Generally, the temperature and flow rate of the drying gas is chosen-so that the polymer/drug-solution droplets are dry enough by the time they reach the wall of the apparatus that they are essentially solid, and so that they form a fine powder and do not stick to the apparatus wall. The actual length of time to achieve this level of dryness depends on the size of the droplets. Droplet sizes generally range from 1 µm to 500 µm in diameter, with 5 to 100 µm being more typical. The large surface-to-volume ratio of the droplets and the large driving force for evaporation of solvent leads to actual drying times of a few seconds or less. This rapid drying is often critical to the particles maintaining a uniform, homogeneous dispersion instead of separating into drug-rich and polymer-rich phase Solidification times should be less than 100 seconds, preferably less than a few seconds, and more preferably less than 1 second. In general, to achieve this rapid solidification of the drug/polymer solution, it is preferred that the size of droplets formed during the spray-drying process are less than 100 µm in diameter, preferably less than 50 µm in diameter, and more preferably less than 25 µm in diameter. The resultant solid particles thus formed are thus generally less than 100 µm in diameter, and preferably less than 50 µm in diameter, and more preferably less than 25 µm in diameter. Typically, particles are 1 to 20 µm in diameter.

Following solidification, the solid powder may stay in the spray-drying chamber for 5 to 60 seconds, further evaporating solvent from the solid powder. The final solvent content of the solid dispersion as it exits the dryer should be low, since this reduces the mobility of drug molecules in the dispersion, thereby improving its stability. Generally, the residual solvent content of the dispersion should be less than 10 wt % and preferably less than 2 wt %. In some cases, it may be preferable to spray a solvent or a solution of a polymer or other excipient into the spray-drying chamber to cause aggregation of the dispersion particles into larger granules so long as the dispersion is not adversely affected.

Spray-drying processes and spray-drying equipment are described generally in Perry's *Chemical Engineers' Handbook*, Sixth Edition (R. H. Perry, D. W. Green, J. O. Maloney, eds.) McGraw-Hill Book Co. 1984, pages 20-54 to 20-57. More details on spray-drying processes and equipment are reviewed by Marshall "Atomization and Spray-Drying," 50 *Chem. Eng. Prog. Monogr. Series* 2 (1954).

Compositions Having Stabilizing and Concentration-Enhancing Polymers

Another aspect of this invention provides a composition that contains a mixture of polymers. The composition comprises a solid dispersion comprising a low-solubility drug and at least a "stabilizing polymer." At least a major portion of the drug is amorphous. The composition also includes a "concentration-enhancing polymer" that increases the maximum measured concentration of the drug in the environment of use (MDC). The concentration-enhancing polymer may, for example, inhibit or slow the rate of precipitation or crystallization of drug from an aqueous solution. The concentration-enhancing polymer may be either part of the dispersion or may be added to the composition after formation of the solid dispersion. The term "concentration-enhancing polymer," generally means any polymer that when present in a dissolution test, as previously described, results in an increase in the maximum concentration of "dissolved drug." As previously described, dissolved drug may be any drug-containing species which is present in the supernatant or filtrate of the dissolution test. The "stabilizing polymer" has a $T_g$ that is greater than that of the concentration-enhancing polymer at relatively high RH, e.g., RH between 30% and 75%. This results in a composition in which the drug has greater stability during storage than a composition containing only the drug and the concentration-enhancing polymer. Together, the combination of the two polymers results in increased bioavailability and increased dispersion stability greater than that achieved by use of the polymers separately.

Polymers suitable for use as the stabilizing polymer include all those which are suitable for use in the solid dispersions of the present invention as described above with the exception of the higher $T_g$ limitation. The stabilizing polymer should be inert and have at least some solubility in water at physiologically relevant H(e.g. pH 1-8).

Where it is desired merely to increase the stability of the composition, the stabilizing polymer may be selected so that it simply has a $T_g$ that is greater than that of the concentration-enhancing polymer at the relevant relative humidity, rather than a $T_g$ in excess of 100° C. at 50% RH. For example, the following polymers may also be used as a stabilizing polymer: hydroxypropyl methyl cellulose acetate succinate, hydroxypropyl methyl cellulose acetate phthalate, hydroxypropyl methyl cellulose acetate, hydroxypropyl methyl cellulose succinate, hydroxypropyl methyl cellulose phthalate, hydroxypropyl methyl cellulose, hydroxypropylcellulose, methyl cellulose, hydroxyethyl cellulose, hydroxyethyl methyl cellulose, hydroxyethyl cellulose acetate, hydroxyethyl ethyl cellulose, hydroxyethyl methyl cellulose acetate succinate, hydroxyethyl methyl cellulose acetate phthalate, carboxymethyl cellulose, and carboxyethyl cellulose. Of course, greater stability will result if the stabilizing polymer is selected so that it has a relatively high $T_g$ at moderate relative humidity, i.e., at least 100° C. at 50% RH.

The optimum amount of stabilizing polymer present in the dispersion will vary depending on such things as the physical properties of the drug (such as its solubility and amorphous $T_g$), the dose of the drug and the type of dosage form to be administered. In general, sufficient stabilizing polymer is added such that the resulting dispersion has sufficient stability that it meets the minium stability criterion for the pharmaceutical product. Typically this is a $T_g$ of 30° C. or higher and preferably a $T_g$ of 50° C. or higher for the dispersion having a typical water content, that is, for dispersions that have-been subjected to a typical storage environment. Also, since bioavailability is also an important criterion, it may be desirable to limit the amount of stabilizing polymer to make room in the formulation for additional concentration enhancing polymer such that an acceptably high in vitro and in vivo MDC and AUC are obtained. In some cases, to obtain the best compromise between stability and bioavailability, the dispersion is formed with only the drug and stabilizing polymer (to maximize stability) and then the concentration-enhancing polymer is dry- or wet-mixed with the dispersion or otherwise added to the dosage form so that the concentration-enhancing polymer does not reduce the $T_g$ of the dispersion thereby compromising its stability.

The concentration-enhancing polymers of the present invention increase the maximum concentration of the drug (MDC) in solution relative to a control composition comprising an equivalent quantity of drug when subjected to the previously described dissolution test. The drug may be dissolved in the form of solvated monomeric molecules or any other drug-containing submicron structure, assembly, aggregate, colloid, or micelle. As used herein, a "use environment" can be either the in vivo environment of the GI tract of an animal, particularly a human, or the in vitro environment of a test solution, such as an MFD solution. A concentration-enhancing polymer can be tested in vivo or, more conveniently, tested in vitro to ascertain whether it is within the scope of the invention. Dissolution tests and in vivo bioavailability tests can be performed as discussed above. The concentration-enhancing polymer should achieve an MDC that exceeds the equilibrium concentration of the undispersed drug in the control composition. Preferably, the concentration-enhancing polymer provides an MDC in a use environment that is at least 1.5-fold that of the MDC provided by a control comprising an equivalent quantity of undispersed drug. For example, if the control composition provides a maximum drug concentration of 1 mg/mL, then the composition including the concentration-enhancing polymer preferably provides a maximum drug concentration of 1.5 mg/mL.

Like the stabilizing polymers, suitable concentration-enhancing polymers should be inert, in that they do not chemically react with the drug in an adverse manner, and should have at least some solubility in aqueous solution at physiologically relevant pHs (e.g., 1-8). Almost any neutral or ionizable polymer that is water-soluble at a pH range of 1-8 may prove to be suitable for a particular drug. One preferred class of polymers is water-soluble cellulosic polymers, and another preferred class is cellulosic polymers which are ionizable, both enterics and so-called non-enterics.

For example, for certain drugs, PVP is known to be effective at inhibiting the precipitation or crystallization of drug from a supersaturated solution. Given PVP's low $T_g$ at high relative humidity (see FIG. 1), amorphous dispersions of drug and PVP are often not sufficiently physically stable to be commercially practical. However, by using both PVP and a stabilizing polymer, the drug may be stabilized and the benefits of PVP may be realized. For example, the drug, PVP and stabilizing polymer such as hydroxypropyl methyl cellulose acetate succinate (HPMCAS), may all be combined to form a single dispersion that has a higher $T_g$ at 50% RH than a dispersion of the drug and PVP alone, and, as a result, improved physical stability. Alternatively, the drug and HPMCAS may be combined to form a dispersion and the PVP may be added to the dosage form, for example, by blending, mixing, or via wet- or dry-granulation or even by coating onto a tablet, bead or capsule. Thus, any method that results in the PVP being present to facilitate the degree of dissolution and inhibit precipitation or crystallization of the drug is suitable. The second embodiment, that is, forming the dispersion from the drug and HPMCAS alone (and adding the PVP to the formulation such that it is not part of the dispersion) is preferred, since, for an equivalent amount of drug and each polymer, the $T_g$ of the dispersion of drug and HPMCAS will generally be higher at 60% RH than a dispersion of drug, HPMCAS, and PVP and therefore is expected to have improved physical stability.

Other concentration-enhancing polymers include: hydroxypropyl methyl cellulose acetate succinate, hydroxypropyl methyl cellulose acetate phthalate, hydroxypropyl methyl cellulose acetate, hydroxypropyl methyl cellulose succinate, hydroxypropyl methyl cellulose phthalate, hydroxypropylmethyl cellulose, hydroxypropylcellulose, methyl cellulose, hydroxyethyl cellulose, hydroxy ethyl methyl cellulose, hydroxy ethyl cellulose acetate, hydroxyethyl ethyl cellulose, hydroxy ethyl methyl cellulose acetate succinate, hydroxyethyl methyl cellulose acetate phthalate, carboxymethyl cellulose, carboxyethyl cellulose, polyvinyl alcohol, polyvinyl alcohol polyvinyl acetate copolymers, polyethylene glycol, polyethylene glycol polypropylene glycol copolymers, polyvinyl pyrrolidone, polyethylene polyvinyl alcohol copolymers, carboxylic acid-functionalized polymethacrylates, amine-functionalized polymethacrylates, chitosan, and chitin.

The composition may take several forms. For example, it may contain a single solid amorphous drug dispersion comprising a mixture of the drug and the two polymers formed by any appropriate process but preferably by solvent processing from a common solvent. In this form, the dispersion is formed, for example, by dissolving the drug and both the stabilizing polymer and the concentration-enhancing polymer in a common solvent. The solvent is then removed to form the solid dispersion, which contains the drug and both polymers.

Alternatively, the composition may contain a solid dispersion comprising the drug and the stabilizing polymer (but not the concentration-enhancing polymer) that is formed by any appropriate method, but preferably solves processing. The solid dispersion is then subsequently dry- or wet-mixed with the concentration-enhancing polymer to form the composition. Mixing processes include physical processing as well as wet-granulation and coating processes. In addition, the composition may contain further additional polymers, selected either to have a high $T_g$ to aid stability or to increase the concentration of the drug upon dissolution, or both.

Alternatively, the low-solubility drug, when dispersed with a stabilizing polymer in a solid-amorphous dispersion, and the concentration-enhancing polymer can also be combined via co-administration of the two components to-a use environment. By co-administration is meant that the solid amorphous dispersion comprised of drug and stabilizing polymer is administered separately from, but within the same general time frame, as the concentration-enhancing polymer. For example, the dispersion can be administered in its own dosage form, that is taken at approximately the same time as the concentration-enhancing polymer, which is in a separate dosage form. The time difference between administration of the drug containing dispersion and the concentration-enhancing polymer is such that they come into physical contact in the use environment. When they are not co-administered at the same time it is generally preferable to administer the concentration-enhancing polymer prior to administration of the drug in the dispersion.

Excipients and Dosage Forms

Although the key ingredients present in the compositions of the present invention are simply the drug to be delivered and the polymer(s), the inclusion of other excipients in the composition, whether included in the solid dispersion or subsequently blended or mixed with the dispersion, may be useful and even preferred. One very useful class of excipients is surfactants. Suitable surfactants include fatty acid and alkyl sulfonates; commercial surfactants such as benzethanium chloride (HYAMINE® 1622, available from Lonza, Inc., Fairlawn, N.J.); DOCUSATE SODIUM (available from Mallinckrodt Spec. Chem., St. Louis, Mo.); polyoxyethylene sorbitan fatty acid esters (TWEEN®, available from ICI Americas Inc., Wilmington, Del.); LIPOSORB® P-20 (available from Lipochem Inc., Patterson N.J.); CAPMUL® POE-0 (available from Abitec Corp., Janesville, Wis.), and natural surfactants such as sodium taurocholic acid, 1-palmitoyl-2-oleoyl-sn-glycero-3-phosphocholine, lecithin, and other phospholipids and mono- and diglycerides. Such materials can advantageously be employed to increase the rate of dissolution by, for example, facilitating wetting, or otherwise increase the MDC attained. These surfactants may comprise up to 10 wt % of the spray-dried dispersion, so long as they do not adversely affect the $T_g$ of the dispersion to the extent that it has unacceptable physical stability.

Addition of pH modifiers such as acids, bases, or buffers may also be beneficial, retarding the dissolution of the dispersion (e.g., acids such as citric acid or succinic acid when the dispersion polymer is anionic) or, alternatively, enhancing the rate of dissolution of the dispersion (e.g., bases such as sodium acetate or amines). Addition of conventional matrix materials, surfactants, fillers, disintegrants, or binders may be added as part of the dispersion itself, added by granulation via wet or mechanical or other means. When such additives are included as part of the dispersion itself, they may be mixed with drug and polymer(s) in the spray-drying solvent, and may or may not dissolve along with the drug and polymer(s) prior to forming the dispersion by spray-drying. These materials may comprise up to 50 wt % of the drug/polymer/additive dispersion, so long as they do not adversely affect the $T_g$ of the dispersion to the extent that it has unacceptable physical stability.

Spray-dried solutions and the resulting dispersions may also contain various additives that aid in the stability, dissolution, tabletting, or processing of the dispersion. Examples of such additives include: surfactants, pH-controlling substances (e.g., acids, bases, buffers), fillers, disintegrators, or binders. Such additives may be added directly to the spray-drying solution such that the additive is dissolved or suspended in the solution as a slurry. Alternatively, such additives may be added following the spraying process to aid in forming the final dosage form.

Other conventional formulation excipients may be employed in the compositions of this invention, including those excipients well-known in the art (e.g., as described in Remington's Pharmaceutical Sciences, Mack Publishing Co., Easton, Pa.). Generally, excipients such as fillers, disintegrating agents, pigments, binders, lubricants, flavorants, and so forth may be used for customary purposes and in typical amounts without adversely affecting the properties of the compositions. These excipients may be utilized after the drug/polymer dispersion has been formed, in order to formulate the dispersion into tablets, capsules, suspensions, powders for suspension, creams, transdermal patches, and the like.

Preferably, compositions of this invention may be used in a wide variety of forms for administration of drugs orally. Exemplary dosage forms are powders or granules that may be taken orally either dry or reconstituted by addition of water to form a paste, slurry, suspension or solution; tablets, capsules, multiparticulates or pills. Various additives may be mixed, ground, or granulated with the compositions of this invention to form a material suitable for the above docage forms. Potentially beneficial additives fall generally into the following classes: other matrix materials or diluents, surfactants, drug complexing agents or solubilizers, fillers, disintegrants, binders, lubricants, and pH modifiers (e.g., acids, bases, or buffers).

Examples of other matrix materials, fillers, or diluents include lactose, mannitol, xylitol, microcrystalline cellulose, calcium diphosphate, starch, polyoxamers such as polyethylene oxide, and hydroxypropyl methyl cellulose.

Examples of surface active agents include sodium lauryl sulfate and polysorbate 80.

Examples of drug complexing agents or solubilizers include the polyethylene glycols, caffeine, xanthene, gentisic acid and cylodextrins.

Examples of disintegrants include sodium starch glycolate, sodium alginate, carboxy methyl cellulose sodium, methyl cellulose, and croscarmellose sodium.

Examples of binders include methyl cellulose, microcrystalline cellulose, starch, and gums such as guar gum, and tragacanth.

Examples of lubricants include magnesium stearate and calcium stearate.

Exemplary pH modifiers include acids such as citric acid, acetic add, ascorbic acid, lactic acid, tartaric acid, aspartic acid, succinic acid, phosphoric acid, and the like; bases such as sodium acetate, potassium acetate, calcium oxide, magnesium oxide, trisodium phosphate, sodium hydroxide, calcium hydroxide, aluminum hydroxide, and the like; and buffers generally comprising mixtures of acids and the salts of said acids. At least one function of inclusion of such pH modifiers is to control the dissolution rate of the drug, polymer, or both, thereby controlling the local drug concentration during dissolution. In some cases it has been determined that the MDC values for some drugs are higher when the solid dispersion dissolves relatively slowly, e.g., over 60 to f80 minutes rather than less than 60 minutes.

In some cases, the dosage form may have superior performance if it is coated with an enteric polymer to prevent or retard dissolution until the dosage form leaves the stomach. Exemplary enteric coating materials include HPMCAS, HPMCP, cellulose acetate phthalate, cellulose acetate trimellitate, carboxylic acid-functionalized polymethacrylates, and carboxylic acid-functionalized polyacrylate.

One dosage form that has been found useful by the inventors for oral administration of the compositions of the present invention is an oral powder for constitution (OPC). The drug-containing composition is prepared by combining the drug and polymers as described above. A first solution containing 0.5 wt % of polyoxyethylene 20 sorbitan monooleate TWEEN 80® (ICI Surfactants, Everberg, Belgium) and 9 wt % polyethylene glycol having a molecular weight of 3350 daltons in water is prepared, and a second solution containing 0.75 wt % of hydroxypropyl cellulose, METHOCEL® (Dow Chemical Company) in water is also prepared. The OPC is prepared by placing the drug-containing composition into a flask and adding 10 mL of the first solution. The flask is shaken for 2 minutes. Then, 20 mL of the second solution is added to the flask and the solution is shaken for another 2 minutes. This OPC can then be orally dosed to a mammal.

In addition to the above additives or excipients, use of any conventional materials and procedures for formulation and preparation of oral dosage forms using the compositions of this invention known by those skilled in the art are potentially useful.

Other features and embodiments of the invention will become apparent from the following examples which are given for illustration of the invention rather than for limiting its intended scope.

EXAMPLE 1

A solution of drug and polymer was made by dissolving 67 mg of the drug [3,6-Dimethyl-2-(2,4,6-trimethyl-phenoxy)-pyridin-4-yl]-(1-ethyl-propyl)-amine hydrogen chloride ("Drug 1," Pfizer, Inc.) and 133 mg of CAP (Eastman, lot # 60616, 35% phthaloyl, 24% acetyl, where the viscosity of a 15 wt % solution in acetone is 50-90 cp) in 15 g of HPLC grade acetone (Aldrich). The drug/polymer solution was then placed in a 20 mL syringe that was then inserted into a syringe pump. (Harvard Apparatus model 22).

Figure 2:
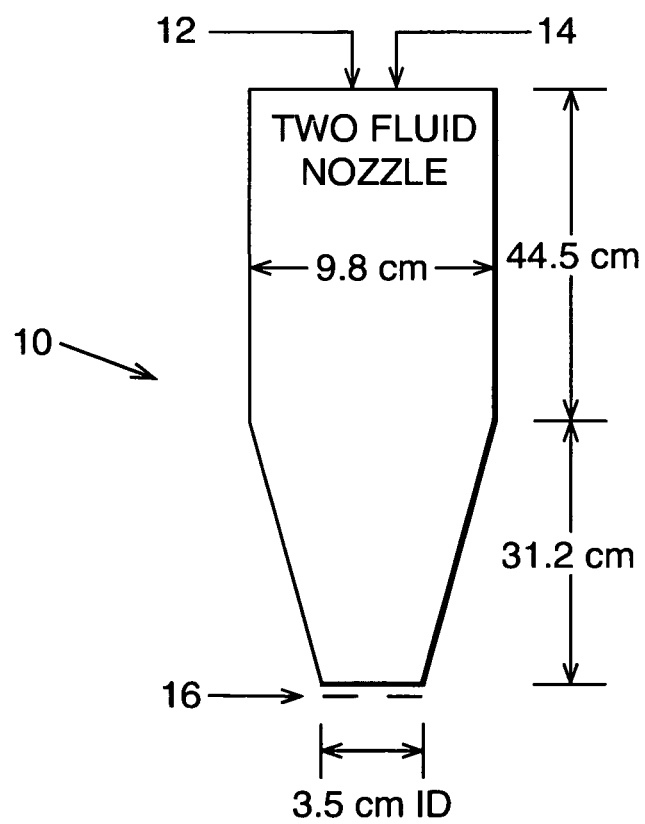
FIG. 2 is a schematic diagram of an exemplary spray-drying apparatus useful in fabricating the solid dispersions of the present invention.

Solvent was rapidly removed from the above solution by spraying it into the spray-drying apparatus schematically shown in FIG. 2, consisting of an atomizer in the top cap of a vertically oriented stainless steel pipe shown generally as 10. The atomizer is a two-fluid nozzle (Spraying Systems Co. 1650) where the atomizing gas is nitrogen, delivered through line 12 to the nozzle at 100° C. and at a flow of 15 g/min, and the solution, at room temperature, is delivered through line 14 to the nozzle at a flow rate of 1.0 g/min using the syringe pump. Filter paper 16 with a supporting screen (not shown) is clamped to the bottom end of the pipe to collect the solid spray-dried material and allow the nitrogen and evaporated solvent to escape. The resulting material was a dry, white, substantially amorphous powder.

EXAMPLES 2-13 AND COMPARATIVE EXAMPLES C1-C8

Examples 2 through-13 and Comparative Examples C1 through C8 were prepared as in Example 1, except that Examples 6 and 7 and Comparative Examples C4 and C5 were prepared with the drug [3,6-Dimethyl-2-(2,4,6-trimethyl-phenoxy)-pyridin-4-yl]-(1-ethyl-propyl)-amine ("Drug 2", Pfizer, Inc.), Example 8 through 11 and Comparative Examples C6 and C7 were prepared with the drug 2-(4-Fluorophenoxy)-N-[4-(1-hydroxy-l-methyl-ethyl)-bezyl] nicotinamide ("Drug 3", Pfizer, Inc.), and Examples 12 and 13 and Comparative Example C8 were prepared using 5-chloro-1H-indole-2-carboxylic acid [(1)-benzyl-2-(3-hydroxy-azetidin-1-yl)-2-oxo-ethyl]-amide ("Drug 4"). Other variables are noted in Table 1.

TABLE 1

| Ex. No. | Drug Mass (mg) | Drug No. | Polymer Mass (mg) | Polymer | Solvent Mass (g) | Solvent | Syringe Size (mL) |
|---|---|---|---|---|---|---|---|
| 1 | 67 | 1 | 133 | CAP | 15 | acetone (HPLC Grade) | 20 |
| 2 | 200 | 1 | 400 | CAT | 60 | acetone (HPLC Grade) | 60 |
| 3 | 30 | 1 | 270 | CAP | 10 | acetone (HPLC Grade) | 20 |
| 4 | 200 | 1 | 300/100 | CAP/PVP | 45 | 1/1 methanol/acetone (HPLC Grade) | 60 |
| 5 | 67 | 1 | 67/67 | CAP/HPMCAS-LF | 15 | acetone (HPLC Grade) | 20 |
| 6 | 67 | 2 | 133 | CAP | 15 | acetone (HPLC Grade) | 20 |
| 7 | 67 | 2 | 67/67 | CAP/HPMCAS-LF | 15 | acetone (HPLC Grade) | 20 |
| 8 | 300 | 3 | 600 | CAT | 30 | acetone | 60 |
| 9 | 150 | 3 | 300 | CAP | 15 | acetone | 20 |
| 10 | 300 | 3 | 600 | HPMCP | 30 | acetone | 60 |
| 11 | 150 | 3 | 300 | PVP:CAP | 15 | 1:1:4 H2O/methanol/acetone | 20 |
| 12 | 150 | 4 | 150 | CAT | 33.3 | 1:1 methanol/acetone | 60 |

TABLE 1-continued

| Ex. No. | Drug Mass (mg) | Drug No. | Polymer Mass (mg) | Polymer | Solvent Mass (g) | Solvent | Syringe Size (mL) |
|---|---|---|---|---|---|---|---|
| 13 | 150 | 4 | 150 | CAP | 33.3 | 1:1 methanol/acetone | 60 |
| C1 | 200 | 1 | 400 | PVP | 45 | 1/1 methanol/acetone (HPLC Grade) | 60 |
| C2 | 30 | 1 | 270 | PVP | 10 | 1/1 methanol/acetone (HPLC Grade) | 20 |
| C3 | 67 | 1 | 133 | HPMCAS-LF | 15 | acetone (HPLC Grade) | 20 |
| C4 | 67 | 2 | 133 | PVP | 20 | 1/1 methanol/acetone (HPLC Grade) | 60 |
| C5 | 150 | 2 | 300 | HPMCAS-LF | 40 | acetone (HPLC Grade) | 60 |
| C6 | 300 | 3 | 600 | HPMCAS-MF | 30 | acetone | 60 |
| C7 | 150 | 3 | 300 | PVP | 15 | 1:9 methanol/acetone | 60 |
| C8 | 150 | 4 | 150 | HPMCAS-LF | 33.3 | methanol | 60 |

COMPARATIVE EXAMPLES C9 AND C10

Comparative examples C9 and C10 were simply 556 mg and 500 mg respectively of Drug 1 and Drug 2 in their equilibrium crystalline state with crystal size of about 1 to 20 μm and 1 to 10 μm, respectively.

EXAMPLE 14

Dissolution performance of the material from Example 1, before exposure to increased temperature and humidity, was measured as follows. In a 37° C. controlled temperature box, 3.0 mg of the material of Example 1 was inserted into a polypropylene microcentrifuge tube (Sorenson Bioscience Inc.). The theoretical MDC in solution (i.e., if all drug dissolved) was 490 μg/ml [(3.0 mg×1000 μg/mg)×(0.33 g drug/g dispersion)×0.90 salt factor×0.98 drug assay/1.8 ml=490 μg/ml]. (This value varies slightly between samples due to small differences in the actual drug assay potency of the samples.) An MFD solution of 1.8 mL of a phosphate buffered saline solution (8.2 mM NaCl, 1.1 mM $Na_2HPO_4$, 4.7 mM $KH_2PO_4$, pH 6.5, 290 mOsm/kg) containing 14.7 mM sodium taurocholic acid and,2.8 mM 1-palmitoyl-2-oleoyl-sn-glycero-3-phosphocholine was added to the tube. The tube was closed and a timer was started. The contents of the tube were then mixed continuously at highest speed on a vortex mixer (Fisher Vortex Genie 2) for 60 seconds. The tube was transferred to a centrifuge (Marathon, Model Micro A), then centrifuged at 13,000G for 60 seconds. A 50 μL-sample was removed from the centrifuge tube by pipette four minutes after the timer was started. Solids in the centrifuge tube were resuspended by mixing the sample continously on the vortex mixer for 30 seconds. The centrifuge tube was returned to the centrifuge and allowed to stand undisturbed until the next sample was taken. Each sample was centrifuged, sampled and resuspended as described, then diluted with 250 μL HPLC grade methanol (Burdick & Jackson) and the concentration of drug was determined by HPLC. Samples were taken after 4, 10, 20, 40, and 90 minutes, analyzed, and drug concentrations for each time point were calculated. The average drug concentration after 4 minutes was 393 μg/mL, after 10 minutes was 409 μg/mL, after 20 minutes was 365 μg/mL, after 40 minutes was 334 μg/mL, and after 90 minutes was 307 μg/mL. Therefore, the MDC for this sample before storage at increased temperature and humidity was 409 μg/mL, comprising the highest average drug concentration observed during the in vitro dissolution test.

In addition, the $AUC_{90}$ value was calculated for Example 1. The $AUC_{90}$ value is the AUC calculated from 0 to 90 minutes. AUC between two individual time points within the curve was determined as follows. First, a straight line was drawn between the two sets of data points $t1$, $c1$ and $t2$, $c2$, where $t1$ and $t2$ are time points and $c1$ and $c2$ are drug concentrations, where $t2>t1$. This defines a geometric area of a trapezoid. The area of this trapezoid is $AUC=c1(t2-t1)+½((t2-t1)×(c2-c1))$. $AUC_{90}$ is determined by calculating the sum of these areas defined by the drug concentrations observed at $t_1$ and $t_2$ equal to: 0 and 4 minutes, 4 and 10 minutes, 10 and 20 minutes, 20 and 40 minutes, and 40 and 90 minutes.

For comparison, the dissolution performance of the crystalline form of the drug in Comparative Example C9 was measured by subjecting a similar quantity of crystalline drug to the same test.

In a similar manner, the other dispersions of Drug 1, formulated as in Examples 2 to 5, were also dissolution-tested. The results of these tests are summarized in Table 2. This data shows that the MDC and $AUC_{90}$ values for the various dispersions of Drug 1 were 2.5-fold to 4-fold higher than for the crystalline drug alone.

In a similar manner, the dispersions of Drug 2, formulated as in Examples 6 and 7, and the crystalline form of Drug 2 in Comparative Example C10 were dissolution-tested. The results of these tests are summarized in Table 3. This data shows that the MDC and $AUC_{90}$ values for the dispersions of Drug 2 were 18-fold to 23-fold higher than for the crystalline drug alone.

TABLE 2

| Example No. | Theoretical MDC (μg/mL) | MDC fresh (μg/mL) | $AUC_{90}$ fresh (μ/mL) |
|---|---|---|---|
| 1 | 490 | 409 | 30,300 |
| 2 | 500 | 340 | 29,000 |
| 3 | 446 | 372 | 28,200 |
| 4 | 527 | 445 | 36,600 |
| 5 | 500 | 446 | 34,200 |
| C9 | 556 | 135 | 9,900 |

TABLE 3

| Example No. | Theoretical MDC (μg/mL) | MDC fresh (μg/mL) | $AUC_{90}$ fresh (μg/mL) |
|---|---|---|---|
| 6 | 475 | 395 | 29,500 |
| 7 | 470 | 396 | 32,700 |
| C10 | 500 | 22 | 1,400 |

EXAMPLE 15

This example demonstrates improved stability of dispersions containing a high $T_g$ polymer. The samples prepared in Examples 1 and 2, and in Comparative Example C1 were stored under elevated temperature and humidity conditions to increase the rate of physical changes occurring in the materials in order to simulate a longer storage interval in a typical storage environment. Analysis of dissolution performance using an in vitro dissolution test and assessment of crystallinity using SEM were done before and after such storage in order to evaluate stability of the dispersion.

Dissolution performance of the material from Example 1, before exposure to increased temperature and humidity, was measured as described in Example 14. The average drug concentration after 4 minutes was 393 µg/mL, after 10 minutes 409 µg/mL, after 20 minutes 365 µg/mL, after 40 minutes 334 µg/mL, and after 90 minutes 307 µg/mL. Therefore, the MDC for this sample before storage at increased temperature and humidity was 409 µg/mL, the highest average drug concentration observed during the in vitro dissolution test.

The materials were then aged in a controlled environment. Approximately 10 mg of the materials prepared in Examples 1 and 2 and Comparative Example C1 were each transferred to a 2 mL glass vial and placed in a vacuum chamber for 16 hours to remove residual solvent from the samples. The vials were then transferred uncapped to a temperature/humidity controlled oven (Environmental Specialties Inc., Model ES2000) at 40° C. and 44% relative humidity and allowed to stand undisturbed for 1 month. Samples were then removed from the oven and transferred to a vacuum dessicator for 16 hours to remove adsorbed water from the samples. The samples were then removed from the vacuum dessicator and tightly capped.

The material from Example 1 was then dissolution tested after the one month storage. The average drug concentration measured after 4 minutes was 390 µg/mL, after 10 minutes 378 µg/mL, after 20 minutes 335 µg/mL, after 40 minutes 315 µg/mL, and after 90 minutes 287 µg/mL. Therefore, the MDC for this sample after storage at increased temperature and humidity was 390 µg/mL. To determine the dissolution performance of the material, the MDC of the material after aging was divided by the MDC of the material before aging (390 µg/mL/409 µg/mL=0.95), thus showing that the MDC of the aged material was 95% of the fresh material.

An analogous procedure was used to assess the dissolution performance of the materials from Examples 2 and C1, before and after exposure to increased temperature and humidity. The results from the tests are summarized in Table 4. Note that the MDC (aged/fresh) of the material from comparative Example C1 was only 0.86, compared with 0.95 for Example 1 and 1.1 for Example 2, the Example 2 measurement demonstrating that the MDC actually improved with aging.

Similarly, the $AUC_{90}$ values for Examples 1 and 2 and Comparative Example C1 were determined. To determine the dissolution performance of the material, the $AUC_{90}$ values of the material after aging was divided by the $AUC_{90}$ of the material before aging. This calculation shows that the $AUC_{90}$ (aged/fresh ratio) for Example 1 was 0.93, for Example 2 was 1.1, for Example C1 was 0.46.

This data demonstrates that the dispersions of Examples 1 and 2 (the dispersions made with high $T_g$ polymers CAP and CAT, respectively), were more stable after exposure to increased temperature and humidity than the dispersion of Comparative Example C1 made from the low $T_g$ (at elevated RH) polymer, PVP.

TABLE 4

| Example No. | MDC fresh (µg/mL) | MDC aged (µg/mL) | Theoretical MDC (µg/mL) | MDC (aged/fresh) | $AUC_{90}$ (aged/fresh) |
|---|---|---|---|---|---|
| 1 | 409 | 390 | 490 | 0.95 | 0.93 |
| 2 | 340 | 395 | 500 | 1.1 | 1.1 |
| C1 | 360 | 309 | 494 | 0.86 | 0.46 |

The materials from Examples 1, 2, and C1 were then assessed for the presence of crystals and changes in particle shape and morphology, before and after exposure to increased temperature and humidity, using SEK analysis as described below. Approximately 0.5 mg of sample was mounted to an aluminum stub with 2-sided carbon tape. The sample was sputter-coated (Hummer Sputtering System, Model 6.2, Anatech Ltd.) with an Au/Pd stage for 10 minutes at 15mV, and studied by SEM. Samples before aging generally appear as spheres or collapsed spheres with smooth and rounded faces and surfaces. Changes in particle appearance indicating physical instability; include: fusing together of individual particles, changes in surface texture, changes in general particle shape, and appearance of straight edges in the particle (indicating possible crystallinity) Scanning electron micrographs of the material from Examples 1 and 2 and Comparative Example C1 before and after exposure to increased temperature and humidity are summarized in Table 5. No significant changes were observed for the materials from Example 1 and 2 after aging. SEM analysis of the sample from Comparative Example C1, however, showed substantial physical changes after aging, including fused particles, greatly increased roughness of the particles, and the presence of straight-edged material present in the particles which may indicate crystallization of drug. This indicates that the dispersions of Examples 1 and 2 were more stable than the dispersion of Comparative Example C1.

TABLE 5

| Example No. | SEM Observations Before Aging | SEM Observations After Aging |
|---|---|---|
| 1 | Smooth collapsed spheres | Smooth collapsed spheres |
| 2 | Smooth collapsed spheres | Smooth collapsed spheres |
| C1 | Smooth spheres | Fused particles Greatly increased roughness of the particles Straight-edged material present |

In addition, samples from Example 1 and Comparative Example C1 were analyzed using powder X-ray diffraction. A sample of material from Example 1 was examined using powder X-ray diffraction before aging. No peaks were observed to indicate crystallinity of the drug. A sample of Example 1 after aging at 40° C./44% RH for one month was also analyzed using powder X-ray diffraction. Again, no peaks were observed to indicate crystallinity of the drug. Comparison of the X-ray diffraction data before and after aging showed no significant differences. Likewise, material from Comparative Example C1 before aging was examined using powder X-ray diffraction and no peaks were observed to indicate crystallinity of the drug. A sample of Comparative Example C1 after aging at 40° C./44% RH for one month was examined using powder X-ray diffraction, and several strong peaks (at scattering angles of 9.5, 16, and 20.5 degrees) were observed indicating crystallization of the drug had occurred. Thus comparison of the powder X-ray diffraction data before and after aging of Comparative Example C1 showed that crystallization-of the drug in Comparative Example C1 had occurred. The powder X-ray diffraction data again shows that the dispersions of Examples 1 and 2 were more stable compared with the dispersion of Comparative Example C1.

EXAMPLE 16

This example demonstrates improved stability of dispersions having a high $T_g$ polymer at low drug loadings. Samples from Example 3 and Comparative Example C2 were stored at 40° C./44% RH for one month using the same procedure as described for the samples in Example 15. In vitro dissolution testing of the samples was done as described in Example 14. These results are summarized in Table 6. Note that the MDC (aged/fresh) of the material from Comparative Example C2 is only 0.92, compared with 0.98 for Example 3. In addition the $AUC_{90}$ (aged/fresh) from C2 is only 0.80, compared with 0.98 for Example 3. This data demonstrates that the dispersion from Example 3 (the dispersion made with a high $T_g$ polymer), is more stable after exposure to increased temperature and humidity than the dispersion from Comparative Example C2.

TABLE 6

| Example No. | MDC fresh (μg/mL) | MDC aged (μg/mL) | Theoretical MDC (μg/mL) | MDC (aged/ fresh) | $AUC_{90}$ (aged/ fresh) |
| --- | --- | --- | --- | --- | --- |
| 3 | 372 | 366 | 446 | 0.98 | 0.98 |
| C2 | 379 | 348 | 474 | 0.92 | 0.80 |

The materials from Example 3 and Comparative Example C2 were assessed for the presence of crystals and changes in particle shape and morphology, before and after exposure to increased temperature and humidity, using scanning electron microscopy analysis as described previously in Example 15. No significant changes were observed for the material from Example 3 after aging. SEM analysis of the samples from Comparative Example C2, however, showed substantial physical changes after aging, including fused particles and the presence of straight-edged material present in the particles, which may indicate crystallization of drug. These results are summarized in Table 7. This demonstrates that the dispersion of Example 3, made from the high $T_g$ polymer CAP, is more stable than the dispersion of Comparative Example C2, made from the polymer PVP.

TABLE 7

| Example No. | SEM Observations Before Aging | SEM Observations After Aging |
| --- | --- | --- |
| 3 | Smooth collapsed spheres | Smooth collapsed spheres |
| C2 | Smooth spheres | Fused particles Straight-edged material present |

EXAMPLE 17

This example demonstrates the stability of a dispersion having both a concentration-enhancing polymer and a high $T_g$ polymer. Samples from Examples 1 and 4, and Comparative Example C1 were stored at 40° C./44% RH for 1 month using the same procedure as described for the samples in Example 15. The dispersion of Example 4 contains both PVP and CAP, while Example 1 contains only CAP and Comparative Example C1 contains only PVP. In vitro dissolution testing of the samples was done as described in Example 14. These results are summarized in Table 8. Note that the MDC (aged/fresh) of the material from Comparative Example C1 is only 0.86, compared with 0.95 for Example 1 and 1.02 for Example 4. Similarly, the $AUC_{90}$ (aged/fresh) of the material from Comparative Example C1 is 0.46, compared with 0.93 and 0.80 for Examples 1 and 4, respectively. This data demonstrates that the dispersion of Example 4 (the dispersion made with a mixture the concentration-enhancing polymer of PVP and the stabilizing polymer CAP), is more stable after exposure to increased temperature and humidity than the dispersion of Comparative Example C1 (the dispersion made with PVP polymer alone). In addition, the MDC of the aged dispersion of Example 4 was higher than the MDC of the aged dispersion of Example 1 indicating improved dissolution performance for the dispersion made with both a concentration-enhancing polymer and a stabilizing polymer.

TABLE 8

| Example No. | MDC fresh (μg/mL) | MDC aged (μg/mL) | Theoretical MDC (μg/mL) | MDC (aged/ fresh) | $AUC_{90}$ (aged/ fresh) |
| --- | --- | --- | --- | --- | --- |
| 4 | 445 | 452 | 527 | 1.02 | 0.80 |
| 1 | 409 | 390 | 490 | 0.95 | 0.93 |
| C1 | 360 | 309 | 494 | 0.86 | 0.46 |

The materials from Examples 1 and 4 and Comparative Example C1 were assessed for the presence of crystals and changes in particle shape and morphology, before and after exposure to increased temperature and humidity, using scanning electron microscopy analysis. The procedure was as described previously in Example 15, except that SEM analysis was performed after 3 days exposure to increased temperature and humidity. No significant changes were observed for the material from Example 1 and Example 4 after three days aging. SEM analysis of the sample from Comparative Example C1, however, shows substantial physical changes after three days aging, including fused particles, rough surfaces on the particle, and the presence of straight-edged material present in the particles, which may indicate crystallization of drug. These results are summarized in Table 9. These results show superior stability of the dispersion in Examples 1 and 4 compared with the dispersion of Comparative Example C1.

TABLE 9

| Example No. | SEM Observations Before Aging | SEM Observations After Aging |
| --- | --- | --- |
| 4 | Smooth collapsed spheres | Smooth collapsed spheres |
| 1 | Smooth collapsed spheres | Smooth collapsed spheres |
| C1 | Smooth spheres | Fused particles Rough particle surfaces Straight-edged material present |

EXAMPLE 18

This example demonstrates the stability of another dispersion (Example 5) having both a high $T_g$ polymer (CAP) and a concentration-enhancing polymer (HPMCAS). Samples from Examples 1 and 5, and Comparative Example C3 were stored at 40° C./44% RH using the same procedure as described for the samples in Example 15, except that the samples were exposed to elevated temperature and humidity for 75 days. ID vitro dissolution testing of the samples was done as described in Example 14. These results are summarized in Table 10. Note that the MDC (aged/fresh) of the material from Comparative Example C3 is only 0.46, compared with 0.87 for Example 1 and 0.88 for Example 5. Similarly, the $AUC_{90}$ (aged/fresh) of the material from Comparative Example C3 is only 0.31, compared with 0.80 for Example 1 and 0.56 for Example 5. This data demonstrates that the dispersion of Example 5 (the dispersion made with a mixture of HPMCAS-LF and CAP polymers), is more stable after exposure to increased temperature and humidity than the dispersion of comparative Example C3 (the material made with HPMCAS-LF polymer alone). This shows that addition of a stabilizing polymer such as CAP to a concentration-enhancing polymer such as HPMCAS results in improved stability.

TABLE 10

| Example No. | MDC fresh (µg/mL) | MDC aged (µg/mL) | Theoretical MDC (µg/mL) | MDC (aged/fresh) | $AUC_{90}$ (aged/fresh) |
|---|---|---|---|---|---|
| 5 | 446 | 355 | 500 | 0.80 | 0.56 |
| 1 | 409 | 354 | 490 | 0.87 | 0.80 |
| C3 | 407 | 189 | 490 | 0.46 | 0.31 |

The materials from Examples 1 and 5, and Comparative Example C3 were assessed for the presence of crystals and changes in particle shape and morphology, before and after exposure to increased temperature and humidity, using scanning electron microscopy analysis. The procedure was as described previously in Example 15, except that SEM analysis was performed after 36 days exposure to increased temperature and humidity. No significant changes were observed for the material from Example 1 and Example 5 after 36 days aging. SEM analysis of the sample from Comparative Example C3, however, shows substantial physical changes after 36 days aging, including fused particles, rough surfaces on the particle, and the presence of straight-edged material present in the particles, which may indicate crystallization of drug. These results are summarized in Table 11. The results show that the dispersions of Examples 1 and 5 are more stable than the dispersion of Comparative Example C3.

TABLE 11

| Example No. | SEM Observations Before Aging | SEM Observations After Aging 36 days at 40° C./44% RH |
|---|---|---|
| 5 | Smooth collapsed spheres | Smooth collapsed spheres |
| 1 | Smooth collapsed spheres | Smooth collapsed spheres |
| C3 | Smooth collapsed spheres | Fused particles Rough particle surfaces Large amounts of straight-edged material present |

EXAMPLE 19

This example demonstrates the stability of dispersions made with a high $T_g$ polymer and Drug 2. Samples from Example 6, and Comparative Examples C4 and C5 were stored at 40° C./44% RH using the same procedure as described for the samples in Example 15, except that the samples were exposed to elevated temperature and humidity for 2 weeks. In vitro dissolution testing of the samples was done as described in Example 14. These results are summarized in Table 12. Note that the MDC (aged/fresh) of the material from Comparative Examples C4 and C5 are 0.45 and 0.52, respectively, compared with 1.1 for Example 6. The $AUC_{90}$ (aged/fresh) of the material from Comparative Examples C4 and C5 are 0.40 and 0.37, respectively, compared with 0.90 for Example 6. This data demonstrates that the dispersion of Example 6 (the dispersion made with CAP polymer), is more stable after exposure to increased temperature and humidity than the dispersions of Comparative Examples C4 and C5 (the dispersions made with PVP or HPMCAS-LF polymers).

TABLE 12

| Example No. | MDC fresh (µg/mL) | MDC aged (µg/mL) | Theoretical MDC (µg/mL) | MDC (aged/fresh) | $AUC_{90}$ (aged/fresh) |
|---|---|---|---|---|---|
| 6 | 395 | 433 | 475 | 1.1 | 0.90 |
| C4 | 488 | 219 | 495 | 0.45 | 0.40 |
| C5 | 410 | 213 | 470 | 0.52 | 0.37 |

The materials from Example 6 and Comparative Examples C4 and C5 were assessed for the presence of crystals and changes in particle shape and morphology, before and after exposure to increased temperature and humidity, using scanning electron microscopy analysis. The procedure was as described previously in Example 15, except that SEM analysis was performed after 2 weeks exposure to increased temperature and humidity. No significant changes were observed for the material from Example 6 after 2 weeks aging. SEM analysis of the samples from Comparative Examples C4 and C5, however, shows substantial physical changes after 2 weeks aging, including fused particles, and the presence of straight-edged material present in the particles, which may indicate crystallization of drug. These results are summarized in Table 13. The results show that the dispersion of Example 6 is more stable than the dispersions of comparative Examples C4 and C5.

TABLE 13

| Example No. | SEM Observations Before Aging | SEM Observations After Aging |
|---|---|---|
| 6 | Smooth collapsed spheres | Smooth collapsed spheres |
| C4 | Smooth spheres | Fused particles |
| C5 | Smooth collapsed spheres | Fused particles Straight-edged material present |

EXAMPLE 20

This example demonstrates the stability of a dispersion (Example 7) having a high $T_g$ polymer (CAP) and a concentration-enhancing polymer (HPMCAS). The samples from Examples 6 and 7, and Comparative Example C5 were stored at 40° C./44% RH using the same procedure as described for the samples in Example 15, except that the samples were exposed to elevated temperature and humidity for 2 weeks. In vitro dissolution testing of the samples was done as described in Example 8. These results are summarized in Table 14. Note that the MDC (aged/fresh) of the material from Comparative Example C5 is 0.52, compared with 1.1 for Example 6 and 0.95 for Example 7. The $AUC_{90}$ (aged/fresh) of -the material from Comparative Example C5 is 0.37, compared with 0.90 for Example 6 and 0.65 for Example 7. This data demonstrates that the dispersion of Example 7 (the dispersion made with a 1:1 ratio mixture of the concentration enhancing polymer HPMCAS-LF and the stabilizing polymer CAP), is more stable after exposure to increased temperature and humidity than the dispersion of Comparative Example C5 (the dispersion made with HPMCAS-LF polymer alone).

TABLE 14

| Example No. | MDC fresh (µg/mL) | MDC aged (µg/mL) | Theoretical MDC (µg/mL) | MDC (aged/ fresh) | AUC (aged/ fresh) |
|---|---|---|---|---|---|
| 6 | 395 | 433 | 475 | 1.1 | 0.90 |
| 7 | 396 | 377 | 470 | 0.95 | 0.65 |
| C5 | 410 | 213 | 470 | 0.52 | 0.37 |

The materials from Example 6, Example 7, and Comparative Example C5 were assessed for the presence of crystals and changes in particle-shape and morphology, before and after exposure to increased temperature and humidity, using scanning electron microscopy analysis. The procedure was as described previously in Example 15, except that SEM analysis was performed after 2 weeks exposure to increased temperature and humidity. No significant changes were observed for the material from Example 6 and Example 7 after 2 weeks aging. SEM analysis of the sample from Comparative Example C5, however, showed substantial physical changes after 2 weeks aging, including fused particles and the presence of straight-edged material present in the particles., which may indicate crystallization of drug. These results are summarized in Table 15. The results show that the dispersion of Examples 6 and 7 are more stable than the dispersion of Comparative Example C5.

TABLE 15

| Example No. | SEM Observations Before Aging | SEM Observations After Aging |
|---|---|---|
| 6 | Smooth collapsed spheres | Smooth collapsed spheres |
| 7 | Smooth collapsed spheres | Smooth collapsed spheres |
| C5 | Smooth collapsed spheres | Fused particles Straight-edged material present |

EXAMPLE 21

This Example discloses the thermal method used to determine $T_g$ of polymeric materials including dispersions of the present invention, at a specific relative humidity. In this method, samples are equilibrated and sealed within an environmental chamber in order to incorporate a specific amount of moisture in the sample. DSC is then used for measurement of the $T_g$.

A sample of material from-Example 1 was equilibrated at 0% RH as follows. Four 30 µl Perkin-Elmer two atmosphere robotic aluminum pans and lids (part # B016-9320) were weighed on a microbalance (Sartorius Model MC5) in pan-lid pairs. Each of the four pan-lid pair weights was recorded to ±1 µg. Approximately 5-10 mg of Example 1 was then placed into each of the four empty pans at ambient temperature and relative humidity. All of these samples (with the lids) were placed in a chamber purged with the boil-off from a liquid nitrogen tank, which resulted in a humidity that was lower than the detection limit of a calibrated humidity sensor. The temperature in the chamber was held in equilibrium with the temperature of the building at approximately 23° C. The samples of Example 1 were left in the chamber for at least 20 hours to completely remove the moisture in the samples.

Once the samples were equilibrated with the 0% RH in the environmental chamber, each sample lid was placed on its corresponding sample pan and crimped with a Perkin-Elmer universal crimper press (part # B013-9005). Crimping each of the samples hermetically seals the sample and ensures that the sample will not absorb any moisture during the course of the experiment. Each sample was weighed on the microbalance and the sample weights were recorded to 0.001 mg.

The $T_g$ was then determined as follows. All $T_g$s were measured with a Perkin-Elmer Pyris 1 differential scanning calorimeter. The heat-flow into and out of the sample was monitored as a function of increasing temperature. As the sample was heated (energy input to the sample) through the glass transition region, a step increase in the heat flow was seen that corresponds to the change in heat capacity of the sample. This region of the heat-flow verses temperature curve was analyzed for the data presented below in Table 16.

All calorimetric experiments on the materials of Example 1 were performed with the following procedure. The crimped samples were placed on the DSC auto-sampling carousel along with an empty pan (care taken not to touch the aluminum pans with bare hands) used for background subtraction. A separate, empty 30 µl aluminum pan was placed in the reference furnace of the DSC to compensate for the teat capacity of the sample pan.

Figure 3:
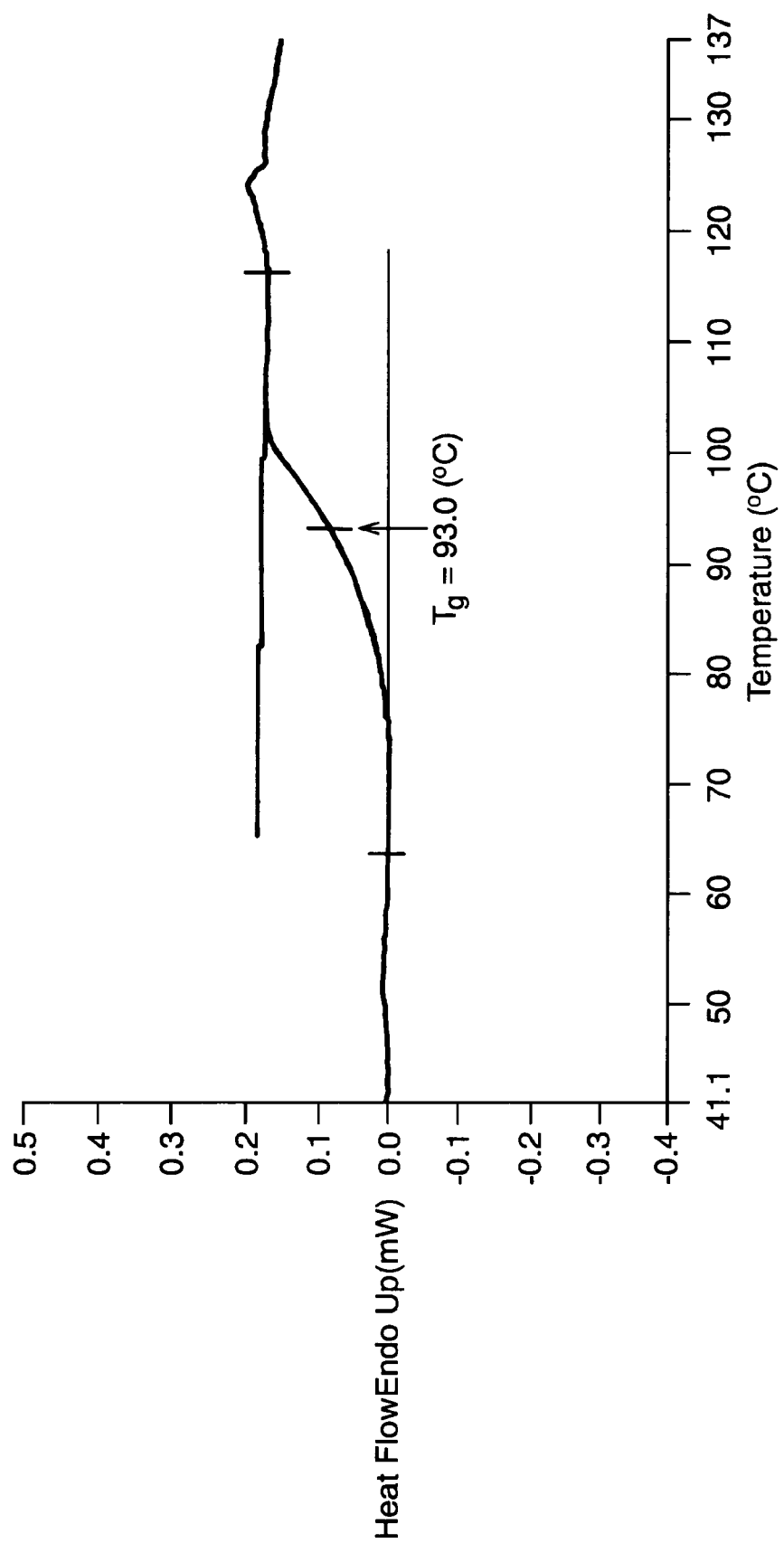
FIG. 3 is a graph of a differential scanning calorimetric trace for Example 1 at 0% relative humidity, showing the measured glass transition temperature as described in Example 15.

The DSC was programmed to load the empty pan and a background scan was heated from 0° C. to 220° C. at 10° C./min. At the end of this scan the empty background pan was removed by the autosampler and the first of the four samples of Example 1 was placed into the sample furnace. This sample was first heated to 100° C. at 10° C./min to remove the thermal history of the sample that could obscure the glass transition (for example, side chain or β transitions). The sample was then cooled back down at approximately 100° C./min to 0° C. and the final thermal scan was run from 0° C. to 175° C. at 10° C./min. FIG. 3 shows the resulting heat flow verses temperature scan in the region of the glass transition along with the coordinates used by the software to measure the $T_g$.

To measure the glass transition, the background scan was subtracted to remove any curvature from the data and then the slope was adjusted to zero so that the glass transition was more easily identifiable. Using the Pyris 1 software, a region bracketing the step change in heat flow (i.e. the $T_g$) was chosen and the tangent lines were adjusted (used by the software to calculated the $T_g$ and the change in heat capacity at the $T_g$) so that they were parallel with the heat flow before and after the $T_g$. The $T_g$ was measured as the temperature at which the heat capacity is one half the total $\Delta C_p$. FIG. 3 shows the resulting scan and measured $T_g$ and $\Delta C_p$ for Example 1 at 0% RH. In some cases, an analogous method was used wherein the integral of a scan such as in FIG. 3 was generated which has the appearance of two intersecting lines with a small amount of curvature near the point of intersection. The $T_g$ was taken as the temperature where the lines intersect. This method is described in *The Physics of Polymers* by Gert Strobl, p. 237-239, Springer-Verlug (1996). Values determined by either method match to within one or two degrees C.

The $T_g$s of the humidified samples were measured in the same way except that the open samples were placed in a humidity chamber to equilibrate with a set humidity. All of the samples from Example 1 (polymer sample in the aluminum pans with the lids) were placed in an environmental chamber (Electro-tech Systems, Inc., model # 518) with the relative humidity held at 50-52% RH by means of a sonic humidifier and controller. These samples were then crimped inside the chamber to seal in the absorbed water and minimize water loss during Tg measurement and run on the Pyris 1 DSC. The resulting calorimetric data was analyzed in the same way as described above to determine the respective $T_g$s. The results are summarized in Table 16.

Glass transition temperatures were also measured for the dispersions of Examples 2 to 11, Comparative Examples C1 to C7 and the polymers CAP, CAT, PVP, and HPMAS-LF following equilibration at 0% RH (dry) and 50% RH in the same manner as is described above for the dispersion of Example 1. The results are summarized in Table 16.

TABLE 16

| Material Designation | $T_g$ (° C.) Dry | 50% RH |
|---|---|---|
| Example 1 | 93 | 56 |
| Example 2 | 92 | 63 |
| Example 3 | 139 | 102 |
| Example 4 | 90 | 57 |
| Example 5 | 89 | 49 |
| Example 6 | 103 | 80 |
| Example 7 | 98 | 76 |
| Example 8 | 136 | 53 |
| Example 9 | 150 | 54 |
| Example 10 | 65 | 46 |
| Example 11 | 138 | 34 |
| Comp. Ex. C1 | 102 | 36 |
| Comp. Ex. C2 | 127 | 44 |
| Comp. Ex. C3 | 80 | 41 |
| Comp. Ex. C4 | 85 | 47 |
| Comp. Ex. C5 | 49 | 39 |
| Comp. Ex. C6 | 51 | 35 |
| Comp. Ex. C7 | 93 | 43 |
| CAP | 176 | 120 |
| CAT | 191 | 118 |
| PVP | 157 | 52 |
| HPMCAS-MF | 119 | 94 |

EXAMPLE 22

This example discloses the utility of the invention with another drug. Samples from Examples 8 through 11, and Comparative Examples C6 and C7 were stored at 40° C./75% RH for 2 weeks using the same procedure as described for the samples in Example 15. In vitro dissolution testing of the samples was done as described in Example 14. These results are summarized in Table 17. The MDC (aged/fresh) of the material from Comparative Example C6 is only 0.87, and the MDC (aged/fresh) of the material from Comparative Example C7 is only 0.27. These two dispersions made with low $T_g$ polymers aged significantly compared to material from Examples 8 through 11, which were made with high $T_g$ polymers. The MDC (aged/fresh) of material from Example 8 is 0.90, the MDC (aged/fresh) of material from Example 9 is 0.94, and the MDC (aged/fresh) of material from Example 10 is 0.95. Similarly, the $AUC_{90}$ (aged/fresh) of C6 and C7 are 0.62 and 0.33, respectively, while $AUC_{90}$ (aged/fresh) for Examples 8, 9, and 10 are 0.90, 1.01, and 0.95. Blending the high $T_g$ CAP with the low $T_g$ PVP (Example 11) improves the stability of the dispersion made with PVP polymer alone (C7).

TABLE 17

| Example No. | MDC Fresh (µg/mL) | MDC Aged (µg/mL) | Theoretical MDC (µg/mL) | MDC (aged/fresh) | $AUC_{90}$ (aged/fresh) |
|---|---|---|---|---|---|
| 8 | 299 | 270 | 301 | 0.90 | 0.90 |
| 9 | 294 | 294 | 301 | 0.94 | 1.01 |
| 10 | 287 | 287 | 304 | 0.95 | 0.95 |
| 11 | 286 | 286 | 300 | 0.54 | 0.50 |
| C6 | 297 | 157 | 301 | 0.87 | 0.62 |
| C7 | 298 | 81 | 314 | 0.27 | 0.33 |

The material from Examples 8 through 11, and Comparative Examples C6 and C7 were assessed for the presence of crystals and changes in particle stape and morphology after exposure to increased temperature and humidity, using scanning electron microscopy analysis. These results are summarized in Table 18.

TABLE 18

| Example No. | SEM Observations After Aging |
|---|---|
| 8 | smooth, collapsed spheres |
| 9 | smooth, collapsed spheres |
| 10 | fused particles |
| 11 | rough particles, straight edges |
| C6 | fused particles, crystals present |
| C7 | many crystals present, fused particles |

Examples 8 and 9 (CAT and CAP dispersions) showed no effects of aging after 2 weeks at 40° C./75% RH. Example 10 (HPMCP dispersion) showed fusing of particles, but no formation of crystals. Example 11 (CAP/PVP blend) showed significant morphological changes, however, obvious crystals were not observed. (The presence of straight-edged material present in the particles may indicate crystallization of drug.) Example 11 can be compared to C7 (drug dispersion with PVP alone), which showed many obvious crystals present. This demonstrates an improvement in stability with the addition of the high $T_g$ polymer. Comparative Example C6 also showed crystals after exposure to increased temperature and humidity.

EXAMPLE 23

This example demonstrates the utility of the invention with another drug. Samples from Examples 12 and 13, and Comparative Example C8 were stored at 40° C./75% RH for 3 months using the same procedure as described for the samples in Example 15. In vitro dissolution testing of the samples was done as described in Example 14. These results are summarized in Table 18. The MDC (aged/fresh) of the material from Comparative Example C8 is only 0.89. This dispersion made with a low $T_g$ polymer aged significantly compared to material from Examples 12 and 13, which were made with high $T_g$ polymers. The MDC (aged/fresh) of material from Example 12 is 1.10, and the MDC (aged/fresh) of material from Example 13 is 1.11. Similarly, the $AUC_{90}$ (aged/fresh) of C8 is 0.76, while $AUC_{90}$ (aged/fresh) for Examples 12 and 13 are 1.05 and 1.10.

TABLE 19

| Example No. | MDC Fresh (μg/mL) | MDC Aged (μg/mL) | Theoretical MDC (μg/mL) | MDC (aged/fresh) | $AUC_{90}$ (aged/fresh) |
|---|---|---|---|---|---|
| 12 | 730 | 802 | 1000 | 1.10 | 1.05 |
| 13 | 708 | 786 | 1000 | 1.11 | 1.10 |
| C8 | 854 | 764 | 1000 | 0.89 | 0.76 |

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

The invention claimed is:

1. A dispersion consisting of a low-solubility drug and cellulose acetate phthalate, wherein said dispersion is formed by spray drying with a non-aqueous solvent in which said drug and said cellulose acetate phthalate are both soluble, and wherein at least 90% of said drug once dispersed in said dispersion is amorphous, said dispersion has a single glass transition temperature of at least 50° C. measured at 50% relative humidity, said composition provides a maximum concentration of said drug in a use environment that is at least 1.5-fold that of a control comprising an equivalent quantity of undispersed drug.

2. The dispersion of claim 1 wherein said low-solubility drug is selected from the group consisting of antihypertensives, antianxiety agents, anticlotting agents, anticonvulsants, blood glucose-lowering agents, decongestants, antihistamines, antitussives, antineoplastics, beta blockers, anti-inflammatories, antipsychotic agents, cognitive enhancers, cholesterol-reducing agents, antiobesity agents, autoimmune disorder agents, anti-impotence agents, antibacterial and antifungal agents, hypnotic agents, anti-Parkinsonism agents, anti-Alzheimer's disease agents, antibiotics, anti-depressants, and antiviral agents.

3. A composition comprising:
(a) the solid dispersion of claim 1 or 2; and
(b) a concentration enhancing polymer selected from the group consisting of hydroxypropyl methyl cellulose acetate succinate, hydroxypropyl methyl cellulose acetate phthalate, hydroxypropyl methyl cellulose acetate, hydroxypropyl methyl cellulose succinate, hydroxypropyl methyl cellulose phthalate, hydroxypropylmethyl cellulose, hydroxypropyl cellulose, methyl cellulose, hydroxyethyl cellulose, hydroxyethyl methyl cellulose, hydroxy ethyl cellulose acetate, hydroxyethyl ethyl cellulose, hydroxy ethyl methyl cellulose acetate succinate, hydroxyethyl methyl cellulose acetate phthalate, carboxymethyl cellulose, carboxyethyl cellulose, polyvinyl alcohol, polyvinyl alcohol polyvinyl acetate copolymers, polyethylene glycol, polyethylene glycol polypropylene glycol copolymers, polyvinyl pyrrolidone, polyethylene polyvinyl alcohol copolymers, carboxylic acid-functionalized polymethacrylates, amine-functionalized polymethacrylates, chitosan, and chitin.

* * * * *